Figure 1:
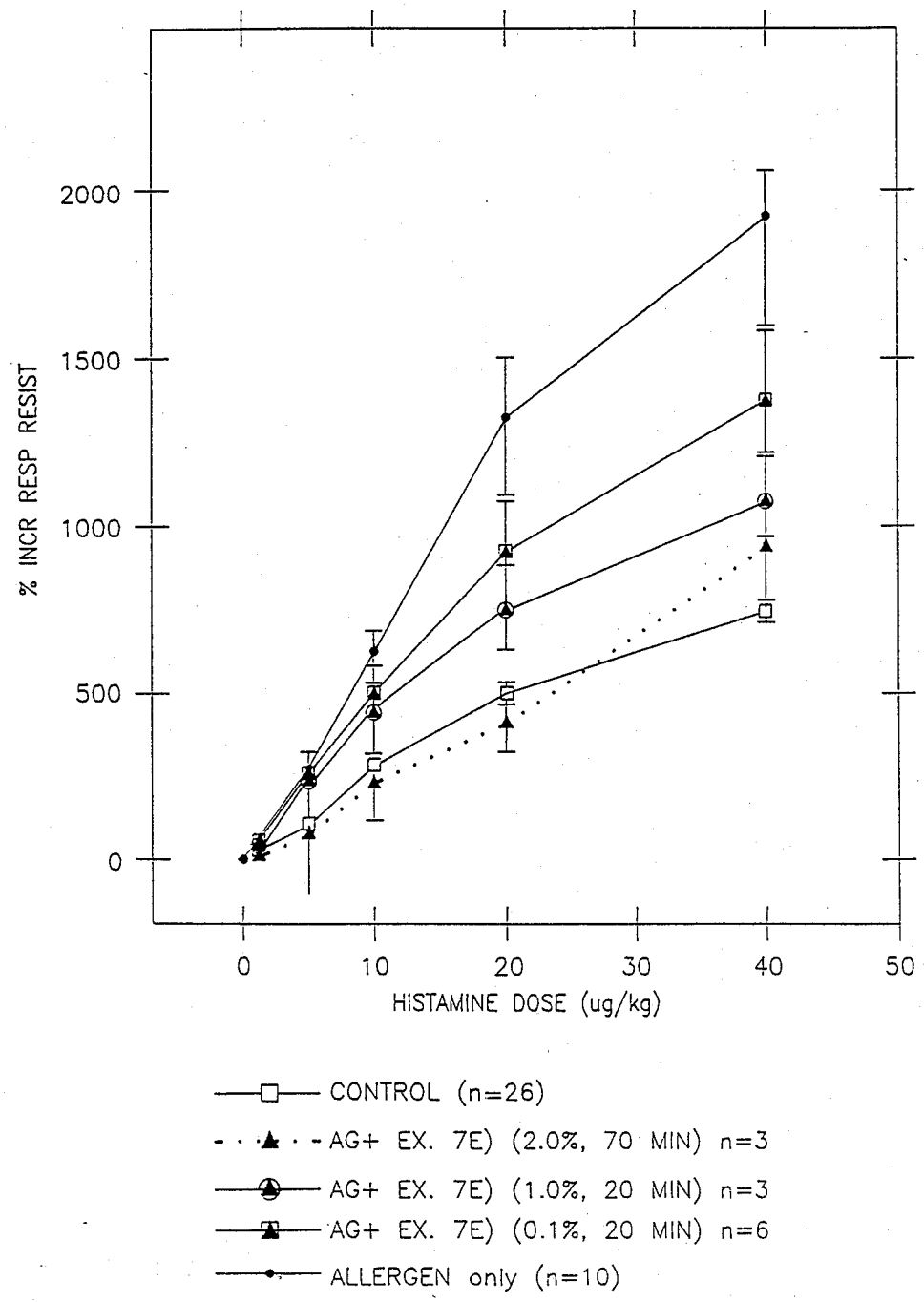

United States Patent [19]

Houlihan

[11] Patent Number: 4,910,206

[45] Date of Patent: Mar. 20, 1990

[54] 5-HETERO-OR ARYL-SUBSTITUTED-IMIDAZO(2,1-A)ISOQUINOLINES AND THEIR USE AS PAF RECEPTOR ANTAGONISTS

[75] Inventor: William J. Houlihan, Mountain Lakes, N.J.

[73] Assignee: Sandoz Pharmaceuticals Corp., E. Hanover, N.J.

[21] Appl. No.: 302,720

[22] Filed: Jan. 27, 1989

Related U.S. Application Data

[63] Continuation-in-part of Ser. No. 226,305, Jun. 29, 1988, abandoned, which is a continuation-in-part of Ser. No. 68,967, Jul. 1, 1987, abandoned, which is a continuation-in-part of Ser. No. 13,515, Feb. 11, 1987, abandoned, which is a continuation-in-part of Ser. No. 885,115, Jul. 14, 1986, abandoned.

[51] Int. Cl.⁴ .............. A61K 31/435; A61K 31/495; C07D 417/02; C07D 471/04
[52] U.S. Cl. .............................. 514/292; 514/228.2; 514/233.2; 514/212; 514/255; 544/60; 544/126; 544/361; 540/599; 546/14; 546/84
[58] Field of Search .................. 546/14, 84; 544/60, 544/126, 361; 514/212, 222, 227, 238, 255, 292, 228.2, 233.2; 540/599

[56] References Cited

U.S. PATENT DOCUMENTS 4,101,553  7/1978  Houlihan .................. 546/84

FOREIGN PATENT DOCUMENTS

88/00587  1/1988  PCT Int'l Appl. .................. 546/84

Primary Examiner—Mary C. Lee
Assistant Examiner—J. Richter
Attorney, Agent, or Firm—Gerald D. Sharkin; Robert S. Honor; Joseph J. Borovian

[57] ABSTRACT

The invention discloses certain 5-hetero or aryl-substituted-imidazo[2,1-a]isoquinolines useful as platelet activating factor (PAF) receptor antagonists, pharmaceutical compositions containing said compounds as an active ingredient thereof and a method of using such compositions for inhibiting PAF-mediated bronchoconstriction and extravassation and PAF-mediated, endotoxin-induced lung injury, and for controlling hyperreactive airways induced by PAF or allergin. In addition, the invention discloses the use of a select group of said compounds as anti-tumor agents.

43 Claims, 1 Drawing Sheet

5-HETERO-OR ARYL-SUBSTITUTED-IMIDAZO(2,1-A)ISOQUINOLINES AND THEIR USE AS PAF RECEPTOR ANTAGONISTS

This application is a continuation-in-part of U.S. patent application Ser. No. 226,305, filed July 29, 1988, now abandoned which in turn is a continuation-in-art of U.S. patent application Ser. No. 68,967, filed July 1, 1987, now abandoned which in turn is a continuation-in-part of U.S. patent application Ser. No. 13,515, filed Feb. 11, 1987, now abandoned which in turn is a continuation-in-part of U.S. patent application Ser. No. 885,115, filed July 14, 1986, now abandoned.

The present invention relates to certain 5-hetero- or aryl-substituted imidazo[2,1-a]isoquinolines and to their use as platelet activating factor (PAF) receptor antagonists. The invention also relates to pharmaceutical compositions containing the afore-mentioned compounds as an active ingredient thereof and to the method of using such compositions for inhibiting PAF-mediated bronchoconstriction and extravasation and PAF-mediated, endotoxin-induced lung injury, and for control of hyperreactive airways induced by PAF or allergen. In addition, the invention relates to the use of a select group of said compounds as anti-tumor agents.

U.S. Pat. No. 3,887,566 discloses certain 2,3-dihydroimidazoisoquinolines exhibiting analgesic, anti-inflammatory, anti-bacterial, anti-viral and cardiovascular properties. U.S. Pat. No. 4,100,165 discloses certain 5-hydroxy-2,3,5,6-tetrahydrofuran imidazo-[2,1-a]isoquinolines containing a pyridyl-, thienyl- or furyl ring in the 5-position, which compounds are useful as anorexics and anti-depressants. U.S. Pat. No. 4,101,553 discloses certain 5-hydrox-2,3,5,6-tetrahydrofuran imidazo[2,1-a]isoquinolines containing an optionally substituted aryl group in the 5-position, said compounds useful as anorexics and anti-depressants.

The essence of the present invention is the discovery that not only are certain 5-hetero- or aryl-substituted-imidazo[2,1-a]isoquinolines useful as PAF receptor antagonists but, in addition, a select group thereof are useful as anti-tumor agents. In one aspect, the present invention involves the use of compounds of formula I:

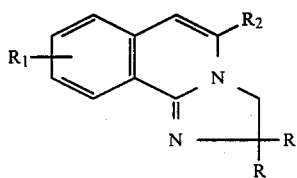

(8- or 9-)

wherein each
R, independently, is hydrogen or methyl;
$R_1$ is hydrogen, chloro, fluoro or $C_{1-3}$alkyl; and
$R_2$ is a member of the group selected from

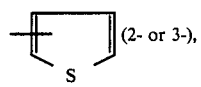

(2- or 3-),

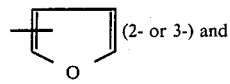

(2- or 3-) and

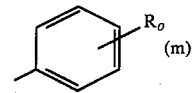

(m)

where
m is 0 or an integer 1 or 2; and
$R_o$ is chloro; fluoro;
straight or branched chain $C_{1-10}$ alkyl;
straight or branched chain $C_{1-10}$ alkoxy;
straight or branched chain $C_{1-10}$ alkylthio;
tri-$C_{1-3}$ alkylsilyl; trifluoromethyl; phenyl;
phenyl monosubstituted by chloro or fluoro; a group of the formula

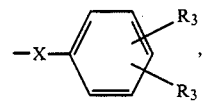

where X is —CH$_2$O—, —OCH$_2$—, —CH$_2$S—, —SCH$_2$—, —CH$_2$—, —CH$_2$CH$_2$—, —CH$_2$OCH$_2$—, —O— or —S— and each $R_3$ is hydrogen, chloro, fluoro $C_{1-4}$alkyl or $C_{1-5}$alkoxy; a group of the formula

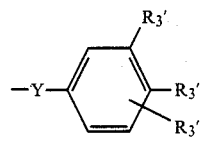

where Y is —O-(CH$_2$)$_{1-5}$, —SCH$_2$—, -(CH$_2$)$_{1-6}$, or —CH$_2$OCH$_2$— and each $R_3'$ is $C_{1-3}$alkoxy; a group of the formula

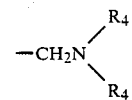

where each $R_4$, independently, is straight or branched chain $C_{1-4}$ alkyl, $C_{5-7}$ cycloalkyl, CH$_2$CH=CH$_2$, a group of the formula

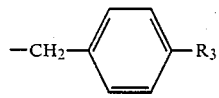

where $R_3$ is as defined above, or the two $R_4$'s together with the nitrogen atom to which they are attached form a group of the formula

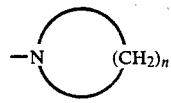

where n is an integer of 4, 5 or 6, or a group of the formula

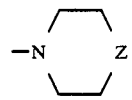

where Z is —O—, —S— or —NCH$_3$; or two R$_o$'s on adjacent carbon atoms form methylenedioxy; with the provisos that: (1) when R$_o$ is other than chloro, fluoro, or straight or branched chain C$_{1-10}$ alkyl, alkoxy or alkylthio, m is 1; and (2) when R$_o$ is other than chloro, fluoro, methyl, methoxy or methylthio, the R$_o$ substituent(s) may only be in the meta or para positions;

and their pharmaceutically acceptable acid addition salts, where such may exist, in inhibiting PAF mediated bronchoconstriction and extravasation and endotoxin-induced lung injury, and for control of hyperreactive airways induced by PAF or allergen.

Of the compounds of formula I, preferred are the compounds of formula I':

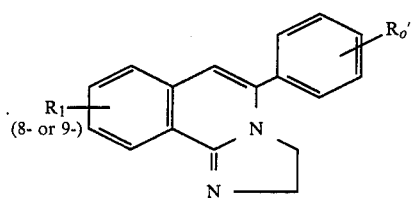

wherein
R$_1$ is as defined above; and
R$_o$' is a group of the formula

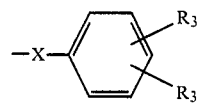

where X and each R$_3$ are as defined above; or a group of the formula

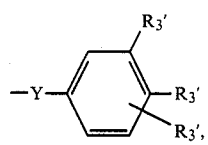

where Y and each R$_3$' are as defined above; with the proviso that the R$_o$' substituent may only be in the meta or para positions;
and their pharmaceutically acceptable acid addition salts, where such may exist.

Another aspect of the present invention involves the novel compounds of formula I, i.e., compounds of formula Ia,

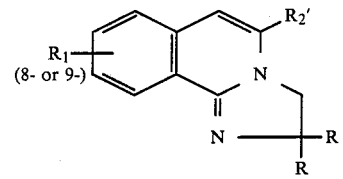

where
R and R$_1$ are as defined above; and
R$_2$' is a member of the group selected from

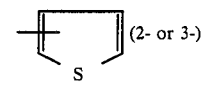

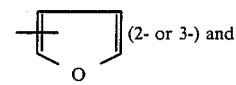

where
m' is an integer 1 or 2; and
R$_o$'' is straight or branched chain C$_{5-10}$ alkyl; straight or branched chain C$_{5-10}$ alkoxy; straight or branched chain C$_{5-10}$ alkylthio; tri-C$_{1-3}$ alkylsilyl; phenyl; phenyl monosubstituted by chloro or fluoro; a group of the formula

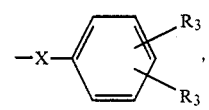

where X and each R$_3$ are as defined above; a group of the formula

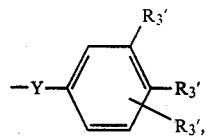

where Y and each R$_3$' are as defined above; or a group of the formula

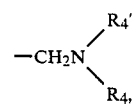

where each R$_4$, independently, is as defined above, with the provisos that:
(1) when R$_o$'' is other than straight or branched chain C$_{5-10}$ alkyl, alkoxy or alkylthio, m' is 1; and
(2) the R$_o$'' substituent(s) may only be in the meta or para positions;
and their pharmaceutically acceptable acid addition salts, where such may exist.

Of the novel compounds of formula Ia, preferred are those of formula Ia',

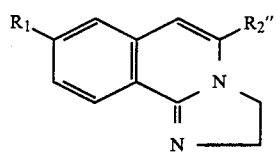 Ia' where
R$_1$ is as defined above; and
R$_2''$ is a member of the group selected from

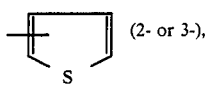 (2- or 3-),

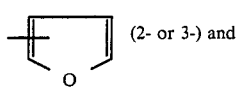 (2- or 3-) and

where R$_o'''$ is tri-C$_{1-3}$ alkylsilyl; a group of the formula

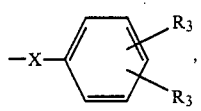, where X and each R$_3$ are as defined above; a group of the formula

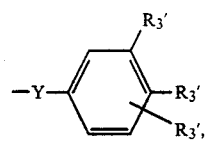, where Y and each R$_3'$ are as defined above; or a group of the formula

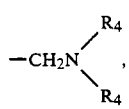, where each R$_4$, independently, is as defined above, with the proviso that the R$_o'''$ substituent may only be in the meta or para positions; and their pharmaceutically acceptable acid addition salts, where such may exist.

Still another aspect of the present invention involves the use of compounds of formula Ib,

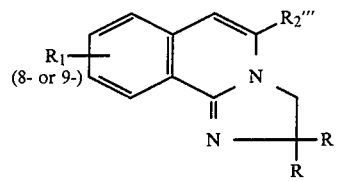 Ib where
R and R$_1$ are as defined above; and
R$_2$ is a member of the group selected from

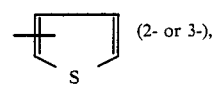 (2- or 3-),

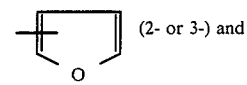 (2- or 3-) and

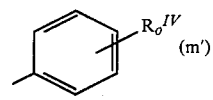

where m' is as defined above; and
R$_o^{IV}$ is chloro; fluoro; straight or branched chain C$_{1-6}$alkyl; tri-C$_{1-3}$alkylsilyl; phenyl; a group of the formula

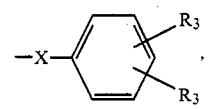, where X and each R$_3$ are as defined above; a group of the formula

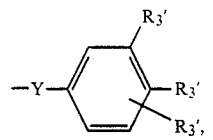, where Y and each R$_3'$ are as defined above; or a group of the formula

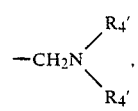, where each R$_4'$ is CH$_2$CH=CH$_2$, or the two R$_4'$'s together with the nitrogen to which they are attached form a group of the formula

where n is as defined above, or a group of the formula

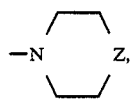

where Z is as defined above; with the provisos that:
(1) when $R_o^{IV}$ is other than chloro, fluoro or $C_{1-6}$alkyl, m' is 1; and (2) when $R_o^{IV}$ is other than chloro, fluoro or methyl, the $R_o^{IV}$ substituent may only be in the meta or para positions;

and their pharmaceutically acceptable acids addition salts, where such may exist, in treating tumors.

Of the compounds of formula Ib, preferred are the compounds of formula Ib',

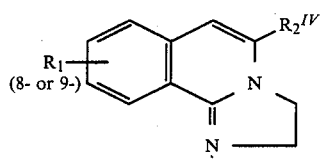

where
$R_1$ is as defined above; and
$R_2^{IV}$ is a group

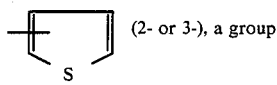 (2- or 3-), a group

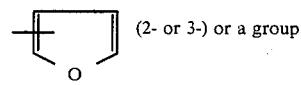 (2- or 3-) or a group

where $R_o^V$ is straight or branched chain $C_{2-6}$alkyl; tri-$C_{1-3}$ alkylsilyl; phenyl; a group of the formula

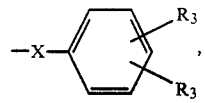

where X and each $R_3$ are as defined above; a group of the formula

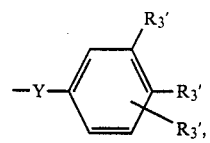

where Y and each $R_3'$ are as defined above; or a group of the formula

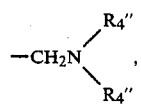

where each $R_4''$ is $CH_2CH=CH_2$, or the two $R_4'''$'s together with the nitrogen to which they are attached form a group of the formula

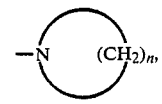

where n is as defined above; with the proviso that the $R_o^V$ substituent may only be in the meta or para positions;

and their pharmaceutically acceptable acid addition salts, where such may exist.

A further aspect of the present invention involves pharmaceutical compositions containing a novel compound of formula Ia as an active ingredient thereof.

The above-identified compounds of formula I may be prepared according to the following reaction scheme:

REACTION A

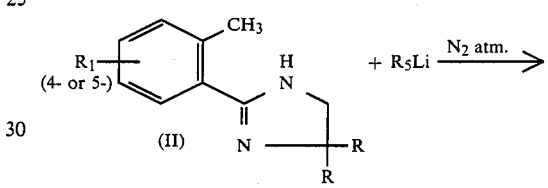

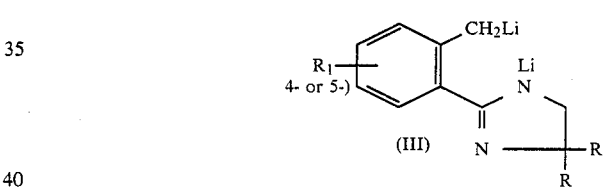

where the R's and $R_1$ are as defined above and $R_5$ is straight or branched chain $C_{1-4}$alkyl.

REACTION B

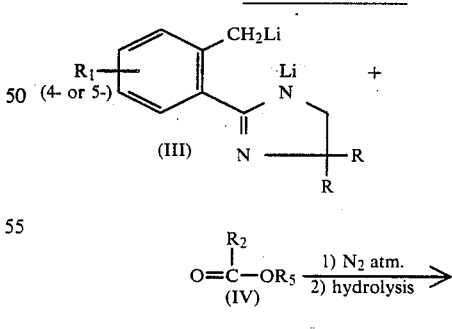

where the R's, $R_1$, $R_2$ and $R_5$ are as defined above.

REACTION C

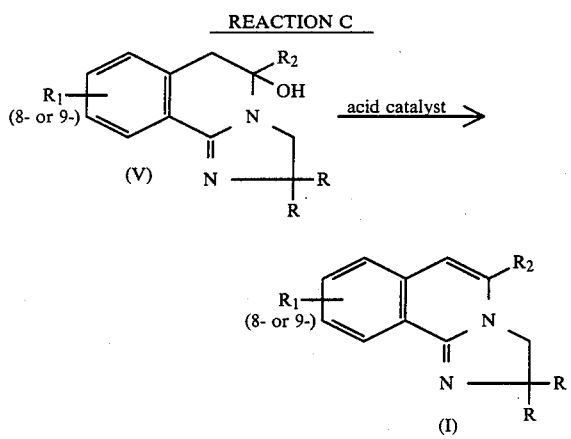

where the R's, $R_1$ and $R_2$ are as defined above.

With respect to the individual reactions, Reaction A concerns the reaction of a compound of formula II with a $C_{1-4}$alkyl lithium compound (preferably straight chained) under a nitrogen atmosphere to yield a compound of formula III. The reaction is generally carried out in the presence of an inert, organic solvent, e.g., an aliphatic hydrocarbon such as heptane, hexane and the like, an aliphatic ether such as diethyl ether, or a cyclic ether such as tetrahydrofuran. As to the temperature and time of the reaction, a temperature in the range of between 25° and 75° C., preferably between 30° and 40° C., for a period of between 30 minutes and 48 hours is most suitable.

Reaction B involves, in a first step, the reaction of a compound produced in Reaction A, i.e., a dilithiated compound of formula III, with a compound of formula IV under a nitrogen atmosphere. As with Reaction A, the first step of Reaction B is conducted in the presence of an aliphatic hydrocarbon such as hexane, heptane and the like, an aliphatic ether such as diethyl ether, or a cyclic ether such as tetrahydrofuran. The first step of Reaction B is conducted at a temperature in the range of $-30°$ to $+50°$ C., preferably $-20°$ to 0° C., for a period of between 30 minutes and 48 hours. The adduct formed is then hydrolyzed in a second step to yield a compound of formula V. The hydrolysis is conducted in conventional manner, e.q., employing water; dilute minoral acid, ammonium chloride solution and the like. The temperature and time of the reaction with respect to hydrolysis is not critical.

In Reaction C, a compound produced in Reaction D, i.e., a compound of formula V, is dehydrated in an inert, organic solvent in the presence of an acid catalyst to yield the desired compound of formula I. The acid catalyst employed can be any mineral acid such as hydrochloric acid, sulfuric acid, phosphoric acid and the like, or an organic acid, e.g., an alkylcarboxylic acid such as acetic acid, an arylcarboxylic acid such as benzoic acid, an alkylsulfonic acid such as methanesulfonic acid or an arylsulfonic acid such as p-toluenesulfonic acid. The preferred acid catalysts are alkylcarboxylic acids, more preferably, acetic acid, and arylsulfonic acids, more preferably, p-toluene-sulfonic acid. The inert solvent is usually an aliphatic hydrocarbon such as hexane; heptane and the like, an aromatic hydrocarbon such as benzene, toluene and the like, a chlorinated hydrocarbon such as chloroform, methylene chloride and the like, an aliphatic ether such as diethyl ether, a cyclic ether such as tetrahydrofuran, or an excess of the acid catalyst, preferably acetic acid or p-toluenesulfonic acid may serve as the solvent. The temperature at which the dehydration is conducted is not critical; however, a temperature in the range of between 35° and 200°. C., preferably between 75° and 120° C., is most suitable. As with the temperature, the time of the reaction is not critical, however, it is preferred that the dehydration be conducted for a period of between 1 and 12 hours, preferably between 1.5 and 4 hours.

The compounds of formula II and IV are either known and obtained by methods described in the literature, or where not known, may be obtained by methods analogous to those described in the literature.

The product of each reaction may, if desired, be purified by conventional techniques such as recrystallization (if a solid), column chromatography, preparative thin layer chromatography, gas chromatography (if sufficiently volatile) or fractional distillation under high vacuum (if sufficiently volatile). Often, however, the crude product of one reaction may be employed in the following reaction without purification.

A still further aspect of the present invention involves the novel compounds of formula V, i.e., the compounds of formula Va:

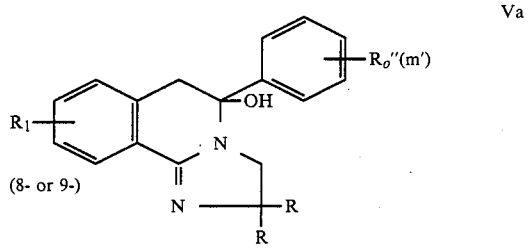

wherein

R, $R_1$, m' and $R_o''$ are as defined above;

and their pharmaceutically acceptable acid addition salts, where such may exist.

As is evident to those skilled in the art, certain of the compounds of formula I and V can exist as stereoisomers and such isomers and their enantiomers are contemplated as being included within the scope of this invention. Moreover, certain of the compounds of formula I and IV can exist as optical isomers and such isomers are also contemplated as being included within the scope of this invention.

As previously indicated, pharmaceutically acceptable acid addition salts (i.e., those salts which do not significantly increas the toxicity of the base compound) of the compounds of formula I and V, where such may exist, are included within the scope of this invention. These include salts of mineral acids such as hydrochloric, hydrobromic, phosphoric and sulfuric acids, as well salts of organic acids such as tartaric, acetic, citric, malic, maleic, methanesulfonic and gluconic acids.

All of the compounds of formulae I, as well as their pharmaceutically acceptable acid addition salts, are useful as platelet activating factor receptor antagonists as indicated by their ability to inhibit specific binding of [$^3$H]-PAF to platelets according to the Human Platelet PAF Receptor Assay test (Test A) as follows:

Human blood is obtained by venipuncture of healthy, human donors into an anti-coagulant mixture containing 3.15% of trisodium citrate and 20 μg/ml of Prostaglandin $I_2$ ($PGI_2$) in a ratio of blood to anti-coagulant of 9:1.

Platelet rich plasma (PRP) is prepared by centrifugation (250×g) of the blood for 20 minutes at room temperature. The PRP is then centrifuged (900×g) for 20 minutes at room temperature and the platelet pellet is washed two times with Tris-Tyrode's (TT) solution having a pH of 7.4 and containing 0.25% bovine serum albumin (BSA), and to which has been added $PGI_2$ at a final concentration of 0.3 µg/ml. The platelets are resuspended at 350,000/µl in TT/BSA containing 1.4 mM $CaCl_2.2H_2O$ and 0.7 mM $MgCl_2.6H_2O$. All of the tests are conducted in duplicate and each of the test compounds is evaluated at concentrations of 100, 50, 1 and 0.1 µM. For each determination, the following solutions are mixed:

500 µl of the above-described platelets;
10 µl of [$^3$H]-PAF (40,000 counts per minute (cpm) to a final concentration of 1.5 µM); and
either
10 µl of the test compound at 50× the desired final concentration,
10 µl of vehicle (total bound), or
10 µl of $1.85 \times 10^{-5}$M cold PAF (non-specifically bound).

Each mixture is allowed to incubate at room temperature for one hour, after which time the reaction is terminated by the addition of 500 µl of ice cold TT/BSA and centrifugation (900×g) at 4° C. for 10 minutes. The resultant supernatant is aspirated into scintillation vials and the pellet is washed with 250 ml. of ice cold TT/BSA and centrifuged (900×g) at 4° C. for 10 minutes. The supernatants are then aspirated into the same scintillation vials as before and 10 ml. of Scintiverse II (a liquid scintillation cocktail) is added to and mixed therewith. The pellets are resuspended in 500 µl of Scintiverse II and mixed well. An additional 2 ml. of Scintiverse II is then added to the vials and, after mixing, the vials are counted for 1 minute in a liquid scintillation spectrometer. The amount of specific binding is calculated as the difference in cpm between the total bound [$^3$H]-PAF and non-specifically bound [$^3$H]-PAF. The percent inhibition of specific binding is determined by dividing the cpm specifically bound in the presence of the test compound by the cpm specifically bound in total, multiplying by 100 and then substracting from 100. An $IC_{50}$ (50% inhibitor concentration) value is generated by evaluating the test compound over the full concentration range.

Moreover, in view of their usefulness as PAF receptor antagonists, the compounds of formula I, and their pharmaceutically acceptable acid addition salts, have been found useful as inhibitors of PAF mediated bronchoconstriction, which property was evaluated by the PAF-Induced Pulmonary Inflation Pressure (PIP) Increase test (Test B) as follows:

Male guinea pigs, weighing between 300 and 400 gm, are anesthetized, after which time trachea tube, carotid and jugular catheters are inserted. The test animal is then force ventilated employing a small animal Harvard respirator and the resistance to lung inflation (PIP) is measured utilizing a pressure transducer and recorder. The test compound is administered either orally at 30 minutes up to 4 hours prior to or parenterally, e.g., intravenously (jugular), intraarterially, intragastrically, etc., at 5 minutes up to 4 hours prior to the introduction of PAF. The PAF ($C_{18}$-Sandoz, Hanover) is dissolved in Tris-Tyrode's bovine serum albumin buffer and administered intravenously (jugular) at 166 µg/kg. Any blood pressure measurements taken are recorded from a transducer attached to the carotid catheter. Two responses are noted in the PIP recordings after the PAF is administered: (1) an immediate response which, in PAF-only treated test animals, averages out to between 70% and 80% more than the baseline PIP values. (This early response is also the greatest response and is, therefore, termed maximal PIP); and (2) the long term (at least 30 minutes) PIP response which slowly decreases to baseline. A reading at 15 minutes after the administration of PAF is termed the endpoint PIP. The effect of the test compound on the PIP response is determined by the difference between the percent increase in maximal PIP over baseline for the test animal to which has been adminstered PAF and the test compound compared to the test animal to which only PAF has been administered.

Furthermore, the compounds of formula I, and their pharmaceutically acceptable acid addition salts, are useful as inhibitors of PAF mediated extravasation (the extrusion of plasma from the lumen of the blood vessels into the vessel wall and surrounding tissues) measured as a function of hemoconcentration according to the PAF-Induced Extravasation test (Test C) as follows:

Male guinea pigs, weighing between 300 and 400 gm, are anesthetized, after which time a femoral catheter is inserted. The test compound is administered either orally or parenterally one hour up to 4 hours prior to the introduction of PAF. The PAF ($C_{18}$-Sandoz, Hanover) is dissolved in Tris-Tyrode's bovine serum albumin buffer and administered intravenously (jugular) at 100 ng/kg.

To determine the hematocrit value, which is employed to index hemoconcentration and is defined as the percent of packed red blood cells in a sample of blood which is centrifuged to separate plasma from the cellular components, blood samples are collected in 50 µl heparinized hematocrit tubes. These samples are taken just prior to the injection of PAF, one minute subsequent to the injection of PAF and every two minutes therefter until 15 minutes has lapsed subsequent to the injection of PAF. The tubes are then centrifuged and the percent of packed red blood cells (hematocrit) is measured (PAF induces a maximal increase in hematocrit at 5 to 7 minutes subsequent to the injection of PAF). The percent increase in hematocrit over the value prior to the injection of PAF is calculated. The hemacrotit values obtained with the test compound are compared to the hemoconcentration values obtained with PAF alone and are expressed as percent inhibition of percent increase in hematocrit.

Still further, the compounds of formula I, and their pharmaceutically acceptable acid addition salts, are useful as inhibitors of PAF-mediated, endotoxin-induced lung injury and, analogously, endotoxin-induced-septic shock and adult respiratory distress syndrome. The ability of the compounds of formula I to inhibit PAF-mediated, endotoxin-induced lung injury can be measured in accordance with the test presented by S. Chang at the 2nd International Conference on *Platelet Activating Factor and Structurally Related Alkyl Ether Lipids* in Gatlinburg, Tenn. on Oct. 26–29, 1986.

Based on previous reports that lung tissue and blood PAF increased to endotoxin-treated rats, it was determined that the intraperitoneal administration of 2 mg/kg of endotoxin (*S. enteritidis*) causes acute lung injury, as assessed by the extravascular accumulation of water and $^{125}$I-albumin in preferred lungs isolated from rats ninety minutes following in vivo endotoxin treatment. Thus, the wet lung/body weight ratio (as an index of lung water content) increases from 5.35±0.48 to 8.26±0.36 and the albumin leak index increases from 0.46±0.09 to 1.01±0.07. In order to measure the effectiveness of a compound as an inhibitor of endotoxin-induced lung injury, the test compound is administered intraperitoneally prior to the in vivo endotoxin treatment.

The ability of the compounds of formula I, and their pharmaceutically acceptable acid addition salts, to inhibit PAF-mediated, endotoxin-induced septic shock can be measured in accordance with the test presented by C. N. Sessler, et al at the Annual Meeting of the American Federation for Clinical Research in New Orleans, La. during January, 1987.

All sheep are prepared for testing employing the Chronic Sheep Lung Lymph preparation which is well documented in the literature, with the modifications that chronic tracheostomies are performed on the test animals and pleural pressure catheters inserted at the time of the initial surgery. All catheters are brought to the outside through stab wounds in the skin, the chest is closed and the test animals are allowed to recover for several days until they appear healthy and lung lymphs are free of blood before experiments are commenced.

In order to measure the effectiveness of a compound as an inhibitor of some of the important hemodynamic effects of endotoxin on septic shock, 1.3 μg/kg of endotoxin or saline is administered to groups of test animals intravenously over a 30 minute period and 200 mg/kg of the test compound or saline is administered intravenously over a five-hour period. The pulmonary arterial pressure (PAP), cardiac output (CO) and partial oxygen pressure ($PO_2$) are monitored continuously over the five-hour period.

The ability of the compounds of formula I, and their pharmaceutically acceptable acid addition salts, to inhibit PAF-mediated, endotoxin-induced adult respiratory distress syndrome can be measured in accordance with the test presented by B. W. Christman, et al at the Annual Meeting of the American Thoracic Society and American Lung Association on May 10th–13th, 1987.

In order to measure the effectiveness of a compound as an inhibitor of some of the important hemodynamic effects of endotoxin on adult respiratory distress syndrome, 0.5 ug/kg of E. coli endotoxin over a 20 minute period, 20 mg/kg/hr of the test compound for 6 hours, or 0.5 ug/kg of E. coli endotoxin 1 hour after commencing 20 mg/kg/hr of the test compound for 6 hours, are administered to groups of test animals intravenously. The pulmonary arterial pressure (PAP), dynamic compliance (DC) of the lungs and lung lymph flow (LLF) are monitored continuously over a five-hour period.

Yet still further, the compounds of formula I, and their pharmaceutically acceptable acid addition salts, are useful in controlling hyperreactive airways induced by PAF or allergen, which property can be measured in accordance with the following procedure (Test D):

Male Hartley guinea pigs weighing 250 gm are sensitized to ovalbumin by aerosol inhalation exposure. The test animals are then subsequently rechallenged with ovalbumin aerosol repeatedly (3 to 6 times) over a period of two to three weeks. Airway reactivity is assessed by an acetylcholine dose response curve at times (1 to 3 days) after the last ovalbumin exposure. The test compound is assessed for its ability to control hyperreactive airways by administering it orally with a gavage tube in an acceptable vehicle prior to each ovalbumin allergen exposure.

Because of their usefulness in controlling hyperreactive airways induced by PAF or allergen when administered orally, the compounds of formula I were assessed for their ability in controlling hyperreactive airways induced by PAF or allergen when administered by the inhalation route employing the following procedure (Test E):

Male Hartley guinea pigs weighing 250 gm are sensitized to ovalbumin (OA) by a series of three peritoneal injections of OA over a period of six weeks. On the day of the study, the test compound is topically (i.e., by inhalation) administered to the test animals by aerosol exposure prior to allergen exposure. The test animals are restrained in a small plexiglas chamber to allow head-only exposure to aerosol administration of the test compound. Aerosol is generated by an ultrasonic nebulizer and the output is directed into the head chamber of the test animal box. The test animals are exposed in this manner for 20 minutes immediately preceding allergen exposure. Allergen exposure consists of 60 minutes of aerosol OA exposure. Airways reactivity is assessed by an allergen dose response curve at 24 hours after allergen exposure.

Employing the above procedure, the ability of the compound of Example 7(E) to control hyperreactive airways was demonstrated by a histamine dose response curve in the following groups of test animals:

Group 1—Control test animals which were neither exposed to the test compound nor to allergen. This group represents baseline airway reactivity.

Group 2—Allergen-only test animals which were not exposed to the test compound but were exposed to aerosol allergen. This group represents the no-drug effect.

Group 3—Test animals which were treated by aerosol exposure to a 2% solution of the test compound in water for 70 minutes prior to allergen exposure.

Group 4—Test animals which were treated by aerosol exposure to a 1% solution of the test compound in water for 20 minutes prior to allergen exposure.

Group 5—Test animals which were treated by aerosol exposure to a 0.1% solution of the test compound in water for 20 minutes prior to allergen exposure.

As can be seen from the results obtained, which are set forth in FIG. 1, the compound of Example 7(E) is effective in controlling allergen-induced hyperreactive airways by the inhalation route.

The compounds of formula I, and their pharmaceutically acceptable acid addition salts, may be administered by any conventional route for use in the recited PAF indications. In particular, the compounds of formula I, and their pharmaceutically acceptable acid addition salts, may be administered enterally, preferably orally, e.g., in the form of tablets or capsules, or parenterally, e.g., in the form of injectable solutions or suspensions. All of such type compositions may be prepared in conventional manner.

As regards to the control of hyperreactive airways, it has been surprisingly found that when a compound of formula I, or a pharmaceutically acceptable acid addition salt thereof, is administered by the inhalation route, the results are superior to those obtained by enteral, e.g., oral, administration. The inhalation mode of administration is particularly suitable because it allows for higher local tissue drug concentration in the organ of interest, e.g., the lung, and results in a much lower total delivered dose, thereby drastically reducing the possibility of systemic toxicity or side effects. Such type compositions may be in conventional form for systemic administration of the active agent through the pulmonary mucous membranes employing conventional pulmonary applicators which may be, e.g., an aerosol for inhalation or a powder spray device for inhalation.

The precise dosage of a compound of formula I, or a pharmaceutically acceptable acid addition salt thereof, to be employed in treating platelet activating factor mediated bronchoconstriction and extravasation and PAF-mediated, endotoxin-induced lung injury, and for controlling hyperreactive airways induced by PAF or allergen depends upon several factors including the host, the nature and severity of the condition being-treated, the mode of administration and the particular compound employed. However, in general, satisfactory inhibition or antagonism of platelet activating factor mediated bronchoconstriction and extravasation and PAF-mediated, endotoxin-induced lung injury and hyperreactive airways control is achieved when a compound of formula I, or a pharmaceutically acceptable acid addition salt thereof, is administered orally at a daily dosage of 0.2–100, preferably 0.2–50 mg/kg body weight or, for most larger primates, a daily dosage of 10–2000 mg, preferably 10–350 mg. A typical oral dosage is 50 or 100 mg, two or three times a day.

The precise dosage of a compound of formula I, or a pharmaceutically acceptable acid addition salt thereof, to be employed in controlling hyperreactive airways by the inhalation route depends upon several factors including the host, the severity of the condition being treated and the particular compound employed. However, in general, satisfactory control of hyperreactive airways by the inhalation route is achieved when a compound of formula I, or a pharmaceutically acceptable acid addition salt thereof, is administered at a dose which is between 10 and 1000 times lower than the oral dose. Satisfactory daily doses for the control of hyperreactive airways by the inhalation route may be determined from the dosage regimen indicated above regarding oral administration.

As indicated above, all of the compounds of formula Ib and their pharmaceutically acceptable acid addition salts, are anti-tumor agents and, therefore, are useful in inhibiting the growth of various lymphomas, sarcomas, myelomas and luekemia cell lines, as indicated by the Tumor Cell Cytotoxicity test (TCC test) as follows:

In flat bottom microtiter plates (Nunc Roskieide, Denmark) were placed Abelson 8.1 tumor cells in DMEM+10% fetal calf serum and the tumor cell-containing plates were incubated with 1, 3 and 5 ug of the test compound for a period of 6 to 72 hours. The number of viable tumor cells present was determined by measuring the alkaline phosphatase in the following manner. The tumor cell plates were centrifuged (500×g.) for ten minutes and the supernatant flicked off. Without further washing, 100 ul of buffer containing 20 ul of diethanolamine, 2 uM of $MgCl_2 6H_2O$, 2.5 uM of p-nitrophenylphosphate and 10 mg Triton X-100 were added. The samples were incubated for 60 minutes at room temperature and the enzymatic reaction was terminated by the addition of 100 ul of 0.5N NaOH. The absorbance was then measured at 405 nM using a Titertek Multiskan apparatus.

The anti-tumor activity of the compounds of formula Ib, and their pharmaceutically acceptable acid addition salts, may also be demonstrated employing the Influence on Cytotoxicity of $ET-18-OCH_3$ test (IC-ET test) as follows: Bone marrow cell macrophages ($10^5$/well) obtained from [BALB/CX57/BL$_6$]Fl mice were incubated with 10 ug of (±)-1-octadecyl-2-methoxy-3-phosphoryl choline ($ET-18-OCH_3$) for 24 hours in flat bottom microtiter plates (Nunc Roskieide, Denmark), after which time they are centrifuged and washed once. Abelson 8.1 tumor cells in DMEM+10% fetal calf serum and 1, 3 and 5 ug of the test compound were then added to the plates. With the cytotoxicity of $ET-18-OCH_3$ (10 ug) alone set at 100%, the inhibition or enhancement of the cytotoxic effect, as measured by an alkaline phosphatase assay, was determined and values recorded after 72 hours for 1, 3 and 5 ug of the test substance.

The usefulness of the compounds of forumula Ib, and their pharmaceutically acceptable acid addition salts, in treating tumors may additionally be demonstrated employing the following procedure:

Meth A fibrosarcoma cells were induced in BALB/C mice by administering methylcholanthrene according to the procedure of Old, et al (L. J. Old, E. A. Boyse, D. A. Clarke, and E. Carswell, Ann. N.Y. Acad. Sci., 101, 80 (1962). These tumor cells were harvested from the peritoneal cavity 10 to 12 days after administration of methylcholanthrene. The $CBF_1$ mice of 10 -12 week age were each implanted with $7.3 \times 10^6$ Meth A sarcoma cells to serve as control. A second group of ten $CBF_1$ mice were each implanted with 7.3 $10^6$ Meth A sarcoma cells and on day one after implant each mouse was treated p.o. with 5–50 ug of the test compound per day for a total of twenty or twenty-seven days. Tumor growth and survivors were assayed on days 7, 14, 21 and 28 after tumor implantation. Under these conditions, none of the control group animals survived, whereas all of the animals which were administered 50 ug per day of the compound of Example 3(N) for 28 days not only survived but showed no evidence of the presence of any tumors as well.

As with the PAF inhibition use, the precise dosage of a compound of formula Ib, or a pharmaceutically acceptable acid addition salt thereof, to be employed for inhibiting tumors depends upon several factors including the host, the nature and the severity of the condition being treated, the mode of administration and the particular compound employed. However, in general, satisfactory inhibition of tumors is achieved when a compound of formula Ib, or a pharmaceutically acceptable acid addition salt, is administered enterally, preferably orally, or parenterally, e.g., intravenously, at a daily dosage of 10–100, preferably 5–35 mg/kg body weight or, for most larger primates, a daily dosage of 500–2000 mg, preferably 1000–1500 mg. A typical oral dosage is 400 mg, two to three times a day, or 20 mg/kg intravenously over a 24 hour period.

Regardless of use, a small dosage is gradually increased until the optimal dosage for the host under treatment is determined. For administration by injection, a dosage somewhat lower than would be used for oral administration of the same compound to the same host having the same condition is usually employed.

A typical dosage unit for oral administration in PAF inhibition may contain 2.5 to 500 mg of a compound of formula I, or a pharmaceutically acceptable acid addition salt thereof, whereas for inhibition of tumors, a typical dosage unit for oral administration may contain 300 to 600 mg of a compound of formula Ib, or a pharmaceutically acceptable acid addition salt thereof. Preferred oral dosage units for PAF inhibition contain 5 to 200 mg, especially 10 to 100 mg of a compound of formula I or a pharmaceutically acceptable acid addition salt thereof, whereas preferred oral dosage units for inhibition of tumors contain 300 to 500 mg, especially 350 to 450 mg of a compound of formula Ib, or a pharmaceutically acceptable acid addition salt thereof.

The compounds of formula I, and their pharmaceutically acceptable acid addition salts thereof, may be formulated into such pharmaceutical compositions containing an amount of the active substance that is effective in treating platelet activating factor mediated bronchoconstriction and extravasation and PAF-mediated, endotoxin-induced lung injury, and for controlling hyperreactive airways induced by PAF or allergen, such compositions in unit dosage form and such compositions comprising a solid pharmaceutically acceptable carrier.

As to the compounds of formula Ib, they may be formulated into such pharmaceutical compositions containing an amount of the active substance that is effective in treating tumors, such compositions in unit dosage form and such compositions comprising a solid pharmaceutically acceptable carrier.

Tablets and capsules containing the ingredients indicated below may be prepared by conventional techniques and are useful in treating platelet activating factor mediated bronchoconstriction and extravasation and PAF-mediated, endotoxin-induced lung injury, and for controlling hyperreactive airways induced by PAF or allergen. The tablet and the capsule may be suitably administered two or three times a day.

| Ingredients | Weight (mg) tablet | capsule |
| --- | --- | --- |
| compound of formula I, e.g., the compound of Example 7E) | 50 | 50 |
| tragacanth | 10 | — |
| lactose (spray-dried) | 212.5 | 100 |
| cornstarch | 15 | — |
| talcum | 10 | — |
| magnesium stearate | 2.5 | — |
| Total | 300.0 | 150.0 |

The following tablets and capsules may be prepared by conventional techniques and are useful as tumor inhibitors. The tablet may be administered two to four times a day whereas the capsule is suitably administered three times a day.

| Ingredients | Weight (mg) tablet | capsule |
| --- | --- | --- |
| compound of formula I, e.g., the compound of Example 3N) | 400 | 400 |
| tragacanth | 10 | — |
| lactose (spray-dried) | 197.5 | 250 |
| corn starch | 25 | — |
| talcum | 15 | — |
| magnesium stearate | 2.5 | — |
| Total | 650.0 | 650 |

The following pharmaceutical compositions are formulated with the indicated amount of active ingredient using conventional techniques. The injectable suspension and the oral suspension represent formulations useful as unit doses and may be administered in treating platelet activating factor mediated bronchoconstriction and extravasation. The injectable suspension may be administered one or twice a day whereas the oral liquid suspension is suitably administered three times a day.

| Ingredients | Weight (mg) sterile injectable suspension | oral liquid suspension |
| --- | --- | --- |
| compound of formula I, e.g. the compound of Example 7E) | 5 | 3 |
| sodium carboxymethylcellulose U.S. Pat. No. | 1 | 8 |
| methyl cellulose | 0.3 | — |
| polyvinylpyrrolidone | 2.7 | — |
| lecithin | 1.5 | — |
| benzyl alcohol | 0.01 | — |
| magnesium aluminum silicate | — | 25 |
| flavor | — | q.s. |
| color | — | q.s. |
| methyl paraben, U.S. Pat. No. | — | 3 |
| propyl paraben, U.S. Pat. No. | — | 0.7 |
| polysorbate 80 (e.g. Tween 80), U.S. Pat. No. | — | 5 |
| sorbitol solution, 70%, U.S. Pat. No. | — | 1450 |
| buffer agent to adjust pH for desired stability | q.s. for injection | q.s. |
| water | q.s. to 1 ml | q.s. to 5 ml |

The preferred pharmaceutical compositions from the standpoint of preparation and ease of administration are solid compositions, particularly liquid or hard-filled capsules and tablets containing from about 10 to 100 mg of the active ingredient concerning the PAF inhibition use and from about 350 to 450 mg of the active ingredient with respect to tumor inhibition.

The following examples show representative compounds encompassed by this invention and their synthesis. More particularly, Examples (1a), (2A), through (2NN), (4A)–(4C), (6A)–(6N), (8), (10A)–(10C) and (12) are directed to compounds of formula V and Examples 1, (3A) through (3NN), (5A)–(5C), (7A)–(7N), (9), (11A)–(11C) and (13) are directed to compounds of formula I. However, it should be understood that they are for purposes of illustration only.

EXAMPLE 1

5-(p-fluorophenyl)-2,3-dihydroimidazo[2,1-a]isoquinoline

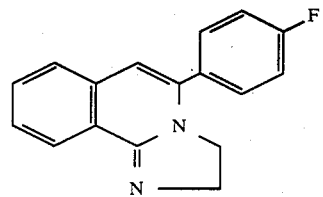

(a) Preparation of
5-(p-fluorophenyl)-2,3,5,6-tetrahydroimidazo[2,1-a]isoquinolin-5-ol Into a flask, maintained under nitrogen and equipped with a stirrer, condenser, and dropping funnel, was charged 6.26 g (0.04 mol) of 2-(o-tolyl)-2(1H)-imidazoline and 100 ml of dry tetrahydrofuran. The solution was stirred, treated with 84 ml of 1.6M n-butyl lithium (0.13 mol) in hexane and maintained at 35° C. for ca. 5 hours. The mixture was treated with 20.7 g (0.16 mol) of ethyl-p-fluorobenzoate in 50 ml of dry tetrahydrofuran and then maintained at 50° C. for ca. 5 hours. The reaction was then cooled in an icebath and treated with 22.8 ml of saturated ammonium chloride. The tetrahydrofuran layer was separated in a separatory funnel, dried with magnesium sulfate, filtered and then concentrated in vacuo. The residue was dissolved in a hot methylene chloridemethanol (1:1) mixture which, upon cooling, yielded the desired compound.

Preparation of the title compound

A solution containing 2.8 g (0.01·mol) of the compound prepared in (a) above and 40 ml of glacial acetic acid was refluxed, with stirring, under a nitrogen atmosphere for ca. 5 hours. The acetic acid was then removed by evaporation in vacuo and the residue treated with 50 ml of water and then made alkaline with 35 ml of 2N sodium carbonate. The mixture was then extracted with two 100 ml portions of methylene chloride, after which time the organic layer was separated, dried over anhydrous magnesium sulfate, filtered and the solvent removed in vacuo. The crude product obtained was recrystallized employing a mixture of methanol and water to yield the desired title compound, m.p. 150°–151° C.

EXAMPLE 2

Following essentially the procedure of Example (1a) above, and using in place of the ethyl-p-fluorobenzoate, an approximately equivalent amount of:
(a) ethyl-p-diethylaminomethylbenzoate;
(b) ethyl-p-chlorobenzoate;
(c) ethyl benzoate;
(d) ethyl-3,4-dimethoxybenzoate;
(e) ethyl-p-methoxybenzoate;
(f) ethyl-3,4-methylenedioxybenzoate;
(g) ethyl-3,4-dichlorobenzoate;
(h) ethyl-2,4-dichlorobenzoate;
(i) ethyl-m-trifluoromethylbenzoate;
(j) ethyl-o-chlorobenzoate;
(k) ethyl-p-methylbenzoate;
(l) ethyl-m-chlorobenzoate;
(m) ethyl-o-fluorobenzoate;
(n) ethyl-p-piperidinomethylbenzoate;
(o) ethyl-p-pyrrolidinomethylbenzoate;
(p) ethyl-p-morpholinomethylbenzoate;
(q) 2-thienyl carboxylic acid ethyl ester;
(r) methyl-p-(2-chloro-4-fluorobenzyloxy)benzoate;
(s) methyl-p-(2,6-dichlorobenzyloxy)benzoate;
(t) ethyl-p-t-butylbenzoate;
(u) ethyl-p-phenylbenzoate;
(v) methyl-p-dibenzylaminomethylbenzoate;
(w) methyl-p-dicyclohexylaminomethylbenzoate;
(x) methyl-p-diisopropylaminomethylbenzoate;
(y) methyl-p-ethylbenzoate;
(z) methyl-p-trimethylsilylbenzoate;
(aa) methyl-p-phenoxybenzoate;
(bb) methyl-p-diallylaminomethylbenzoate;
(cc) methyl-p-benzyloxybenzoate;
(dd) ethyl fuorate;
(ee) methyl-p-thiomorpholinomethylbenzoate;
(ff) methyl-m-t-butylbenzoate;
(gg) methyl-p-(2,6-dichlorophenoxymethyl)benzoate;
(hh) methyl-p-(3,4,5-trimethoxybenzyloxy)benzoate;
(ii) methyl-p-(2-fluorobenzyloxy)benzoate;
(jj) methyl-p-(4-fluorobenzyloxy)benzoate;
(kk) methyl-p-(2-chlorobenzyloxy)benzoate;
(ll) methyl-p-(2-chloro-6-fluorobenzyloxy)benzoate;
(mm) methyl-p-(2,4-dichlorobenzyloxy)benzoate; and
(nn) methyl-p-(4-t-butylbenzyloxy)benzoate;

there was obtained
(A) 5-(4-diethylamino)methylphenyl]-2,3,5,6-tetrahydroimidazol[2,1-a]isoquinolin-5ol;
(B) 5-(p-chlorophenyl)-2,3,5,6,-tetrahydroimidazo[2,1-a]isoquinolin-5-ol;
(C) 5-phenyl-2,3,5,6-tetrahydroimidazo[2,1-a]isoquinolin-5-ol;
(D) 5-(3,4-dimethoxyphenyl)-2,3,5,6-tetrahydroimidazo[2,1-a]isoquinolin-5-ol;
(E) 5-(4-methoxyphenyl)-2,3,5,6,-tetrahydroimidazo[2,1-a]isoquinolin-5-ol;
(F) 5-(3,4-methylenedioxyphenyl)-2,3,5,6-tetrahydroimidazo[2,1-a]isoquinolin-5-ol;
(G) 5-(3,4-dichlorophenyl)-2,3,5,6-tetrahydroimidazo[2,1-a]isoquinolin-5-ol;
(H) 5-(2,4-dichlorophenyl)-2,3,5,6-tetrahydroimidazo[2,1-a]isoquinolin-5-ol;
(I) 5-(3-trifluoromethylphenyl)-2,3,5,6-tetrahydroimidazo[2,1-a]isoquinolin-5-ol;
(J) 5-(2-chlorophenyl)-2,3,5,6-tetrahydroimidazo[2,1-a]isoquinolin-5-ol;
(K) 5-(4-methylphenyl)-2,3,5,6-tetrahydroimidazo[2,1-a]isoquinolin-5-ol;
(L) 5-(chlorophenyl-2,3,5,6-tetrahydroimidazo[2,1-a]isoquinolin-5-ol;
(M) 5-(2-fluorophenyl)-2,3,5,6-tetrahydroimidazo[2,1-a]isoquinolin-5-ol;
(N) 5(4-piperidinomethylphenyl)-2,3,5,6-tetrahydroimidazo[2,1-a]isoquinolin-5-ol;
(O) 5-(4-pyrrolidinomethylphenyl)-2,3,5,6-tetrahydroimidazo[2,1-a]isoquinolin-5-ol;
(P) 5-(4-morpholinomethylphenyl)-2,3,5,6-tetrahydroimidazo[2,1-a]isoquinolin-5-ol;
(Q) 5-(2-thienyl)-2,3,5,6-tetrahydroimdazo[2,1-a]isoquinolin-5-ol;
(R) 5-[4'-(2-chloro-4-fluorobenzyloxy)phenyl]-2,3,5,6-tetrahydroimidazo[2,1-a]isoquinolin-5-ol;
(S) 5-[4'-(2,6-dichlorobenzyloxy)phenyl]-2,3,5,6-tetrahydroimidazo[2,1-a]isoquinolin-5-ol;
(T) 5-(4-t-butylphenyl)-2,3,5,6-tetrahydroimidazo[2,1-a]isoquinolin-5-ol;
(U) 5-(4-phenylphenyl)-2,3,5,6-tetrahydroimidazo[2,1-a]isoquinolin-5-ol;
(V) 5-(4-dibenzylaminomethylphenyl)-2,3,5,6-tetrahydroimidazo[2,1-a]isoquinolin-5-ol;
(W) 5-(4'-dicyclohexylaminomethylphenyl)-2,3,5,6-tetrahydroimidazo[2,1-a]isoquinolin-5-ol;
(X) 5-(4'-diisopropylaminomethylphenyl)-2,3,5,6-tetrahydroimidazo[2,1-a)isoquinolin-5-ol;
(Y) 5-(4'-ethylphenyl)-2,3,5,6-tetrahydroimidazo[2,1-a]isoquinolin-5-ol;
(Z) 5-(4'-trimethylsilyphenyl)-2,3,5,6-tetrahydroimidazo[2,1-a]isoquinolin-5-ol;
(AA) 5-(4'-phenoxyphenyl)-2,3,5,6-tetrahydroimidazo[2,1-a]isoquinolin-5-ol;
(BB) 5-(4'-diallylaminomethylphenyl)-2,3,5,6-tetrahydroimidazo[2,1-a]isoquinolin-5-ol;
(CC) 5-(4'-benzyloxyphenyl)-2,3,5,6-tetrahydroimdazo[2,1-a]isoquinolin-5-ol;
(DD) 5-(2'-furyl)-2,3,5,6-tetrahydroimidazo[2,1-a]isoquinolin-5-ol;
(EE) 5-(4'-thiomorpholinomethylphenyl)-2,3,5,6-tetrahydroimidazo[2,1-a]isoquinolin-5-ol;
(FF) 5-(3'-t-butylphenyl)-2,3,5,6-tetrahydroimidazo[2,1-a]isoquinolin-5-ol;
(GG) 5-[4'-(2,6-dichlorophenyloxymethyl)phenyl]-2,3,5,6-tetrahydroimidazo[2,1-a]isoquinolin-5-ol;

(HH) 5-[4'-(3,4,5-trimethoxybenzyloxy)phenyl]-2,3,5,6-tetrahydroimidazo[2,1-a]isoquinolin-5-ol;
(II) 5-[4'-(2-fluorobenzyloxy)phenyl]-2,3,5,6-tetrahydroimidazo[2,1-a]isoquinolin-5-ol;
(JJ) 5-[4'-(4-fluorobenzyloxy)phenyl)-2,3,5,6-tetrahydroimidazo[2,1-a]isoquinolin-5-ol;
(KK) 5-[4'-(2-chlorobenzyloxy)phenyl]-2,3,5,6-tetrahydroimidazo[2,1-a]isoquinolin-5-ol;
(LL) 5-[4'-(2-chloro-6-fluorobenzyloxy)phenyl]-2,3,5,6-tetrahydroimidazo[2,1-a]isoquinolin-5-ol;
(MM) 5-[4'-(2,4-dichlorobenzyloxy)phenyl]-2,3,5,6-tetrahydroimidazo[2,1-a]isoquinolin-5-ol; and
(NN) 5-[4'-(4-t-butylbenzyloxy)phenyl]-2,3,5,6-tetrahydroimidazo[2,1-a]isoquinolin-5-ol;
respectively.

EXAMPLE 3

Following essentially the last step of the procedure in preparing the compound of Example 1, and using in place of the compound of Example (1a), an approximately equivalent amount of the compounds of Examples (2A) through (2NN), respectively, there was obtained (A) 5-[4'-(diethylamino)methylphenyl)-2,3,-dihydroimidazo[2,1-a]isoquinoline dihydrochloride, m.p. 292°–294° C.
Test A-IC$_{50}$ 23.5 μM
Test B-81.3% inh. at 100 mg/kg p.o.
(a) 5-(p-chlorophenyl)-2,3-dihydroimidazo[2,1-a]isoquinoline, m.p. >250° C.
Test A-IC$_{50}$ 37.2 μM
TCC test-99% inh. at 5 ug
IC-ET test-98% enh. at 5 ug
(C) 5-phenyl-2,3-dihydroimidazo[2,1-a]isoquinoline, m.p. 143°–145° C.,
Test A-IC$_{50}$ 11.2 μM
Test B-56.7% inh. at 10 mg/kg i.g.
(D) 5-(3',4'-dimethoxyphenyl)-2,3-dihydroimidazo[2,1-a]isoquinoline, m.p., 158°–160° C.
(E) 5-(4'-methoxyphenyl)-2,3-dihydroimidazo[2,1-a]isoquinoline, m.p. 126°–128° C.
(F) 5-(3',4'-methylenedioxyphenyl)-2,3-dihydroimidazo[2,1-a]isoquinoline, m.p. 128°–130° C.
Test A-IC$_{50}$ 19.0 μM
(G) 5-(3',4'-dichlorophenyl)-2,3-dihydroimidazo[2,1-a]isoquinoline, m.p. 158°–160° C.
Test A-IC$_{50}$ 17.0 μM
TCC test-98.6% inh at 5 ug
IC-ET test-99.3% enh. at 5 ug
(H) 5-(2',4'-dichlorophenyl)-2,3-dihydroimidazo[2,1-a]isoquinoline, m.p. 150°–152° C.
Test B-43% inh. at 20 mg/kg i.v.
TCC test-98% inh. at 5 ug
IC-ET-99.1% enh. at 5 ug
(I) 5-(3'-trifluoromethylphenyl)-2,3-dihydroimidazo[2,1-a]isoquinoline, m.p. >250° C.
Test A-IC$_{50}$ 19.2 μM
Test B-11.5% inh. at 10 mg/kg i.g.
Test C-18.8% inh. at 10 mg/kg i.g.
(J) 5-(2'-chlorophenyl)-2,3-dihydroimidazo[2,1-a]isoquinoline, m.p. 134°–136° C.
TCC test-96% inh. at 5 ug
IC-ET test-98% enh. at 5 ug
(K) 5-(p-methylphenyl)-2,3-dihydroimidazo[2,1-a]isoquinoline, m.p. >250° C.
Test A-IC$_{50}$ 5.4 μM
Test B-37.6% inh. at 10 mg/kg i.g.
Test C-43.7% inh. at 10 mg/kg i.g.
TCC test-93% inh. at 5 ug
IC-ET test-91% enh. at 5 ug.
(L) 5-(3'-chlorophenyl)-2,3-dihydroimidazo[2,1-a]isoquinoline, m.p. >250° C.
Test A-IC$_{50}$ 5.4 μM
TCC test-70% inh. at 5 ug
IC-ET test-78% enh. at 5 ug
(M) 5-(2'-fluorophenyl)-2,3-dihydroimidazo[2,1-a]isoquinoline, m.p >250° C.
Test A-IC$_{50}$ 5.7 μM
Test B-21.0% inh. at 10 mg/kg i.g.
Test C-24.0% inh. at 10 mg/kg i.g.
TCC test-69% inh. at 5 ug
IC-ET test-79% enh. at 5 ug
(N) 5-(4'-piperidinomethylphenyl)-2,3-dihydroimidazo[2,1-a]isoquinoline dihydrochloride, m.p. 317°–320° C.
Test A-IC$_{50}$ 12.7 μM
Test B-80.4% inh. at 10 mg/kg i.g.
Test C-64.7% inh. at 10 mg/kg i.g.
TCC test-97% inh. at 5 μg
(O) 5-(4'-pyrrolidinomethylphenyl)-2,3-dihydroimidazo[2,1-a]isoquinoline, m.p. 106°–108° C.
Test A-IC$_{50}$ 59.4 μM
Test B-75.4% inh. at 10 mg/kg i.g.
TCC test-98.7% inh. at 5 μg.
IC-ET test-99.2% enh. at 5 μg.
(P) 5-(4'-morpholinomethylphenyl)-2,3-dihydroimidazo[2,1-a]isoquinoline, m.p. 160°–162° C.
Test B-37% inh. at 20 mg/kg i.v.
(Q) 5-(2-thienyl)-2,3-dihydroimidazo[2,1-a]isoquinoline, m.p. 98°–100° C.
TCC test-98% inh. at 5 μg
IC-ET test-98% enh. at 5 μg
(R) 5-[4'-(2-chloro-4-fluorobenzyloxy)phenyl]-2,3-dihydroimidazo[2,1-a]isoquinoline hydrochloride, m.p. 252°–254° C. (dec.)
Test A-IC$_{50}$ 0.23 μM
Test B-36.4% inh. at 2 mg/kg p.o.
Test C-48.1% inh. at 20 mg/kg p.o.
TCC test-99.1% inh. at 5 μg.
IC-ET test-98.8% enh. at 5 μg
(S) 5-[4'-2,6-dichlorobenzyloxy)phenyl]-2,3-dihydroimidazo[2,1-a]isoquinoline hydrochloride, m.p. 277°–280° C.
Test A-IC$_{50}$ -0.56 μM
Test B-6.3% inh. at 10 mg/kg p.o.
Test C-32.1% inh. at 10 mg/kg p.o.
TCC test 98.7% inh. at 5 μg
IC-ET test-97.9% enh. at 5 μg
(T) 5-(4'-t-butylphenyl)-2,3-dihydroimidazo[2,1-a]isoquinoline, m.p.>200° C.
Test A-IC$_{50}$ 0.8 μM
Test B-50.2% inh. at 10 mg/kg i.v.
Test C-52% inh. at 20 mg/kg p.o.
TCC test-99.7% inh. at 5 μg
IC-ET test-99.5% enh. at 5 μg
(U) 5-(4-phenylphenyl)-2,3-dihydroimidazo[2,1-a]isoquinoline, m.p. >200° C.
Test A-IC$_{50}$ 3.5 μM
Test B-31.8% inh. at 10 mg/kg i.g.
Test C-31.2% inh. at 10 mg/kg i.g.
TCC test-98.6% inh. at 5 μg
IC-ET test-97.2% enh. at 5 μg
(V) 5-(4'-dibenzylaminomethylphenyl)-2,3-dihydroimidazo[2,1-a]isoquinoline dihydrochloride, m.p. 225° C.
Test A-IC$_{50}$ 1.3 μM Test B-43% inh. at 2.43 mg/kg i.a.
Test C-50% inh. at 20 mg/kg p.o.
(W) 5-(4'-dicyclohexylaminomethylphenyl)-2,3-dihydroimidazo[2,1-a]isoquinoline dihydrochloride, m.p. 273° C. (dec.)
  Test A-IC$_{50}$ 13.1 μM
  Test C-44% inh. at 20 mg/kg p.o.
(X) 5-(4'-diisopropylaminomethylphenyl)-2,3-dihydroimidazo[2,1-a]isoquinoline dihydrochloride, monohydrate, m.p. 264° C. (dec.)
  Test A-IC$_{50}$ 81.9 μM
(Y) 5-(4'-ethylphenyl)-2,3-dihydroimidazo[2,1-a]isoquinoline hydrochloride, m.p. 298°-300° C.
  Test A-IC$_{50}$ 6.3 μM
  Test C-11.1% inh. at 20 mg/kg p.o.
  TCC test-98% inh. at 5 μg
  IC-ET test-99.5% enh. at 5 μg
(Z) 5-(4'-trimethylsilyphenyl)-2,3-dihydroimidazo[2,1-a]isoquinoline hydrochloride, m.p. >270° C.
  Test A-IC$_{50}$ 6.5 μM
  Test C-26.3% inh. at 20 mg/kg p.o.
  TCC test-99.5% inh. at 5 μg
  IC-ET test-99.5% enh. at 5 μg
(AA) 5-(4'-phenoxyphenyl)-2,3-dihydroimidazo[2,1-a]isoquinoline hydrochloride, m.p. >270° C.
  Test A-IC$_{50}$ 2.8 μM
  Test C-18.6% inh. at 20 mg/kg p.o.
(BB) 5-(4'-diallylaminomethylphenyl)-2,3-dihydroimidazo[2,1-a]isoquinoline dihydrochloride, m.p. 228° C.
  Test A-IC$_{50}$ 9.2 μM
  Test C-63% inh. at 20 mg/kg p.o.
  TCC test-99% inh. at 5 μg
  IC-ET test-97% enh. at 5 μg
(CC) 5-(4'-benzyloxyphenyl)-2,3-dihydroimidazo[2,1-a]isoquinoline hydrochloride, m.p. 213°-215° C.
  Test A-IC$_{50}$ 0.85 μM
  Test C-35% inh. at 20 mg/kg p.o.
(DD) 5-(2'-furyl)-2,3-dihydroimidazo[2,1-a]isoquinoline dihydrochloride, m.p. >315° C.
  TCC test-98% inh. at 5 μg
  IC-ET test-99% enh. at 5 μg
(EE) 5-(4'-thiomorpholinomethylphenyl)-2,3-dihydroimidazo[2,1-a]isoquinoline dihydrochloride, m.p. 275°-278° C.
  Test A-IC$_{50}$ 1.1 μM
  Test C-30% inh. at 20 mg/kg p.o.
  TCC test-86.8% inh. at 5 μg.
  IC-ET test-84.5% enh. at 5 μg.
(FF) 5-(3'-t-butylphenyl)-2,3-dihydroimidazo[2,1-a]isoquinoline hydrochloride, m.p. 290° C.
  Test A-IC$_{50}$ 4.0 μM
  Test C-28% inh. at 20 mg/kg/p.o.
  TCC test-99.5% inh. at 5 μg
  IC-ET test-99.5% enh. at 5 μg
(GG) 5-[4'-(2,6-dichlorophenyloxylmethyl)phenyl]-2,3-dihydroimidazo[2,1-a]isoquinoline hydrochloride, m.p. 242° C.
  Test A-IC$_{50}$ 0.64 μM
  Test B-52.1% inh. at 20 mg/kg p.o.
  Test C-11.7% inh. at 20 mg/kg p.o.
  TCC test-98% inh. at 5 μg
  IC-ET test-97.9% enh. at 5 μg.
(HH) 5-[4'-(3,4,5-trimethoxybenzyloxy)phenyl]-2,3-dihydroimidazo2,1-a]isoquinoline hydrochloride, m.p. 204°-207° C.
  Test A-IC$_{50}$ 0.15 μM
  Test B-86% inh. at 20 mg/kg p.o.
  Test C-83% inh. at 20 mg/kg p.o.
  TCC test-99.2% inh. at 5 μg.
  IC-ET test-99.9% enh. at 5 μg.
(II) 5-[4'-(2-fluorobenzyloxy)phenyl]-2,3-dihydroimidazo[2,1-a]isoquinoline hydrochloride, m.p. 253°-254° C. (dec.)
  Test A-IC$_{50}$ 0.15 μM
  Test B-42.6% inh. at 20 mg/kg p.o. (at 2 hr. pre-dose)
  Test C-21.6% inh. at 20 mg/kg p.o. (at 2 hr. pre-dose)
  TCC test-99.1% inch. at 5 μg.
  IC-ET test-98.8% enh. at 5 μg
(JJ) 5-[4'-(4-fluorobenzyloxy)phenyl]-2,3-dihydroimidazo[2,1-a]isoquinoline hydrochloride, m.p. 257°-258° C. (dec.)
  Test A-IC$_{50}$ 0.66 μM
  TCC test-99.2% inh. at 5 μg
  IC-ET test-98.8% enh. at 5 μg
(KK) 5-[4'-(2-chlorobenzyloxy)phenyl]-2,3-dihydroimidazo[2,1-a[isoquinoline hydrochloride, m.p. 272° C. (dec.)
  Test A-IC$_{50}$ 0.35 μM
  Test B-79.4% inh. at 20 mg/kg p.o. (at 3 hr pre-dose)
  Test C-33.2% inh. at 20 mg/kg p.o. (at 3 hr. pre-dose)
  TCC test-99.3% inh. at 5 μg
  IC-ET test-99.1% enh. at 5 μg.
(LL) 5-[4'-(2-chloro-6-fluorobenzyloxy)phenyl]-2,3-dihydroimidazo[2,1-a]isoquinoline hydrochloride, m.p >250° C.
  Test A-IC$_{50}$ 0.22 μM
  Test B-44.6% inh. at 20 mg/kg p.o. (at 3 hr. pre-dose)
  Test C-44.6% inh. at 20 mg/kg p.o. (at 3 hr. pre-dose)
  TCC test-98.6% inh. at 5 μg
  IC-ET test-97.2% enh. at 5 μg.
(MM) 5-[4'(2,4-dichlorobenzyloxy)phenyl]-2,3-dihydroimidazo[2,1-a]isoquinoline hydrochloride, m.p. 254° C. (dec.)
  Test A-IC$_{50}$ 0.38 μM
  Test B-63.8% inh. at 20 mg/kg p.o.
  Test C-45.0% inh. at 20 mg/kg p.o.
  TCC test-98.5% inh. at 5 μg
  IC-ET test-97.4% enh. at 5 μg, and
(NN) 5-[4'-(4-t-butylbenzyloxy)phenyl]-2,3-dihydroimidazo[2,1-a]isoquinoline hydrochloride, m.p. 271° C. (dec.)
  Test A-IC$_{50}$ 0.5 μM
  Test B-11.7% inh. at 20 mg/kg p.o. (at 3 hr. pre-dose)
  Test C-46.6% inh. at 20 mg/k p.o. (at 3 hr. pre-dose
  TCC test-99.2% inh. at 5 μg
  IC-ET test-98.9% enh. at 5 μl g, respectively.

EXAMPLE 4

Following essentially the procedure of Example (1a) above, and using in place of 2-(o-tolyl)-2(1H)-imidazoline, an approximately equivalent amount of:
(a) 2-(4-chloro-2-tolyl)-2(1H)-imidazoline;
(b) 2-(5-chloro-2-tolyl)-2(1H)-imidazoline; and
(c) 2-(p-xylyl)-2(1H)-imidazoline;
and using in place of the ethyl-p-fluorobenzoate, an approximately equivalent amount of:
(aa) methyl-p-t-butylbenzoate;
(bb) methyl-p-t-butylbenzoate; and
(cc) methyl-p-t-butylbenzoate;
there was obtained
(A) 5-(4'-t-butylphenyl)-8-chloro-2,3,5,6-tetrahydroimidazo[2,1-a]isoquinolin-5-ol;
(B) 5-(4'-t-butylphenyl)-9-chloro-2,3,5,6-tetrahydroimidazo[2,1-a]isoquinolin-5-ol; and (C) 5-(4'-t-butylphenyl)-9-methyl-2,3,5,6-tetrahydroimidazo[2,1-a]isoquinolin-5-ol, respectively.

EXAMPLE 5

Following essentially the last step of the procedure in preparing the compound of Example 1, and using in place of the compound of Example (1a), an approximately equivalent amount of the compounds of Examples (4A) through (4C), respectively, there was obtained (A) 5-(4'-t-butylphenyl)-8-chloro-2,3-dihydroimidazo[2,1-a]isoquinoline hydrochloride, m.p. >250° C.
Test A-IC$_{50}$ 2.2 μM
Test B-17.4% 17.4% inh. at 20 mg/kg p.o.
Test C-46% inh. at 20 mg/kg p.o.
TCC test-98.5% inh. at 5 μg.
IC-ET test-96.9% enh. at 5 μg.

(B) 5-(4'-t-butylphenyl)-9-chloro-2,3-dihydroimidazo[2,1-a]isoquinoline hydrochloride, m.p. >298° C.
Test A-IC$_{50}$ 40.4 μM
Test C-28% inh. at 20 mg/kg p.o., and (C) 5-(4'-t-butylphenyl)-9-methyl-2,3-dihydroimidazo[2,1-a]isoquinoline hydrochloride, m.p. >275° C.
Test A-IC$_{50}$ 31.8 μM
TCC test-98% inh. at 5 μg
IC-ET test-98% enh. at 5 μg
respectively.

EXAMPLE 6

Following essentially the procedure of Example (1a) above, and using in place of the ethyl-p-fluorobenzoate, an approximately equivalent amount of:
(a) methyl-p-(3,4,5-trimethoxybenzyloxymethyl)benzoate;
(b) methyl-p-(3,4-methoxybenzyloxy)benzoate;
(c) methyl-m-(3,4,5-trimethoxybenzyloxy)benzoate;
(d) methyl-o-(3,4,5-trimethoxybenzyloxy)benzoate;
(e) methyl-p-(3,4,5-trimethoxyphenylethyl)benzoate;
(f) methyl-m-(3,4,5-trimethoxyphenylethyl)benzoate;
(g) methyl-p-(3,4-dimethoxyphenylethyl)benzoate;
(h) methyl-p-(2-methoxyphenylethyl)benzoate;
(i) methyl-p-(4-methoxybenzyloxy)benzoate;
(j) methyl-p-(3,4-dimethylbenzyloxy)benzoate;
(k) methyl-p-(3,4,5-trimethoxyphenylpropyl)benzoate;
(l) methyl-p-(2,3,4-trimethoxybenzyloxy)benzoate;
(m) methyl-p-(3-methoxy-4-pentoxyphenylethyl)benzoate; and
(n) methyl-p-(3,4,5-trimethoxybenzyl)benzoate;
there was obtained
(A) 5-[4'-(3,4,5-trimethoxybenzyloxymethyl)phenyl]-2,3,5,6-tetrahydroimidazo[2,1-a]isoquinolin-5-ol;
(B) 5-[4'-(3,4-dimethoxybenzyloxy)phenyl]-2,3,5,6-tetrahydroimidazo[2,1-a]isoquinolin-5-ol, m.p. 144°-147° C. (dec.);
(C) 5-[3-(3,4,5-trimethoxybenzyloxy)phenyl]-2,3,5,6-tetrahydroimidazo[2,1-a]isoquinolin-5-ol, m.p. 127°-129° C.;
(D) 5-[2-(3,4,5-trimethoxybenzyloxy)phenyl]-2,3,5,6-tetrahydroimidazo[2,1-a]isoquinolin-5-ol;
(E) 5-[4'-(3,4,5-trimethoxyphenylethyl)phenyl]-2,3,5,6-tetrahydroimidazo[2,1-a]isoquinolin-5-ol;
(F) 5-[3'-(3,4,5-trimethoxyphenylethyl)phenyl]-2,3,5,6-tetrahydroimidazo[2,1-a]isoquinolin-5-ol;
(G) 5-[4'-(3,4-dimethoxyphenylethyl)phenyl]-2,3,5,6-tetrahydroimidazo[2,1-a]isoquinolin-5-ol;
(H) 5-[4'-(2-methoxyphenylethyl)phenyl]-2,3,5,6-tetrahydroimidazo[2,1-a]isoquinolin-5-ol;
(I) 5-[4'-(methoxybenzyloxy)phenyl]-2,3,5,6-tetrahydroimidazo[2,1-a]isoquinolin-5-ol, m.p. 180°-182° C.;
(J) 5-[40'-(3,4-dimethylbenzyloxy)phenyl]-2,3,5,6-tetrahydroimidazo[2,1-a]isoquinolin-5-ol;
(K) 5-[4'-(3,4,5-trimethoxyphenylpropyl)phenyl]-2,3,5,6-tetrahydroimidazo[2,1-a]isoquinolin-5-ol;
(L) 5-[4'-(2,3,4-trimethoxybenzyloxy)phenyl]-2,3,5,6-tetrahydroimidazo[2,1-a]isoquinolin-5-ol;
(M) 5-[4'-(3-methoxy-4-pentoxyphenylethyl)phenyl]-2,3,5,6-tetrahydroimidazo[2,1-a]isoquinolin-5-ol, m.p. 157°-159° C.; and
(N) 5-[4-(3,4,5-trimethoxybenzyl)phenyl]-2,3,5,6-tetrahydroimidazo[2,1-a]isoquinolin-5-ol; respectively.

EXAMPLE 7

Following essentially the last step of the procedure in preparing the compound of Example 1, and using in place of the compound of Example (1a), an approximately equivalent amount of the compounds of Examples (6A) through (6N), respectively, there was obtained
(A) 5-[4'-(3,4,5-trimethoxybenzyloxymethyl)phenyl]-2,3-dihydroimidazo[2,1-a]isoquinoline hydrochloride, m.p.>240° C. (dec.)
Test A-IC$_{50}$ 0.11 μM
Test B-42.2% inh. at 20 mg/kg p.o.
Test C-52.2% inh. at 20 mg/kg p.o.
TCC test-92.2% inh. at 5 ug
IC-ET test-92% enh. at 5 ug
(B) 5-[4'-(3,4-dimethoxybenzyloxy)phenyl]-2,3-dihydroimidazo[2,1-a]isoquinoline hydrochloride, monohydrate, m.p.>239° C. (dec.)
Test A-IC$_{50}$ 0.20 μM
Test B-41.5% inh. at 20 mg/kg p.o.
Test C-42.7% inh. at 20 mg/kg p.o.
TCC test-99.4% inh. at 5 ug
IC-ET test-99.9% enh. at 5 ug
(C) 5-[3-(3,4,5-trimethoxybenzyloxy)phenyl]-2,3-dihydroimidazo[2,1-a]isoquinoline hydrochloride, m.p. 238° C.
Test A-IC$_{50}$ 0.74 μM
Test B-64.2% inh. at 20 mg/kg p.o.
Test C-88.0% inh. at 20 mg/kg p.o.
TCC test-99.2% inh. at 5 ug
IC-ET test-99.9% enh. at 5 ug
(D) 5-[2-(3,4,5-trimethoxybenzyloxy)phenyl]-2,3-dihydroimidazo[2,1-a]isoquinoline hydrochloride, m.p. 252° C.
Test A-IC$_{50}$ 26.0 μM
TCC test-98.5% inh. at 5 ug
IC-ET test-99% enh. at 5 ug
(E) 5-[4'-(3,4,5-trimethoxyphenylethyl)phenyl]-2,3-dihydroimidazo[2,1-a]isoquinoline hydrochloride, m.p. 243°-245° C.
Test A-IC$_{50}$ 0.06 μM
Test B-ED$_{50}$ 5.0 mg/kg p.o.
Test C-ED$_{50}$ 4.2 mg/kg p.o.
TCC test-99% inh. at 5 ug
IC-ET test-99% enh. at 5 ug
(F) 5-[3-(3,4,5-trimethoxyphenylethyl)phenyl]-2,3-dihydroimidazo[2,1-a]isoquinoline hydrochloride, m.p. 260°-261° C.
Test A-IC$_{50}$ 0.08 μM
Test B-71.3% inh. at 20 mg/kg p.o.
Test C-67.7% inh. at 20 mg/kg p.o.
TCC test-99.3% inh. at 5 ug IC-ET test-99.9% enh. at 5 ug
(C) 5-[4-(3,4-dimethoxyphenylethyl)phenyl]-2,3-dihydroimidazo[2,1-a]isoquinoline hydrochloride, m.p. 263°-265° C.
Test A-IC$_{50}$ 0.03 μM
Test B-46.3% inh. at 10 mg/kg p.o.
Test C-62.1% inh. at 10 mg/kg p.o.
TCC test-85% inh. at 5 ug
IC-ET test-65% enh. at 5 ug
(H) 5-[4'-(2-methoxyphenylethyl)phenyl]-2,3-dihydroimidazo[2,1-a]isoquinoline hydrochloride, m.p. >270° C.
Test A-IC$_{50}$ 0.03 μM
Test B-53.4% inh. at 20 mg/kg p.o.
Test C-28.0% inh. at 20 mg/kg p.o.
(I) 5-[4'-(4-methoxybenzyloxy)phenyl]-2,3-dihydroimidazo[2,1-a]isoquinoline hydrochloride, m.p. >250° C.
Test A-IC$_{50}$ 0.47 μM
Test B-18.0inh. at 20 mg/kg p.o.
Test C-15.8% inh. at 20 mg/kg p.o.
(J) 5-[4'-(3,4-dimethylbenzyloxy)phenyl]-2,3-dihydroimidazo[2,1-a]isoquinoline hydrochloride, m.p. >270° C.
Test A-IC$_{50}$ 0.2 μM
(K) 5-[40'-(3,4,5-trimethoxyphenylpropyl)phenyl]-2,3-dihydroimidazo[2,1-a]isoquinoline hydrochloride, m.p. 242°-244° C.
Test A-IC$_{50}$ 0.3 μM
(L) 5-[4'-(2,3,4-trimethoxybenzyloxy)phenyl]-2,3-dihydroimidazo[2,1-a]isoquinoline hydrochloride, m.p.>240° C.
Test A-IC$_{50}$ 0.16 μM
(M) 5-[4'-(3-methoxy-4-pentoxyphenylethyl)phenyl]-2,3-dihydroimidazo[2,1-a]isoquinoline hydrochloride, m.p. 260° C. (dec.)
Test A-IC$_{50}$ 1.0 μM, and
(N) 5-[4'-(3,4,5-trimethoxybenzyl)phenyl]-2,3-dihydroimidazo[2,1-a]isoquinoline hydrochloride, m.p. 238°-240° C.
respectively.

EXAMPLE 8

Following essentially the procedure of Example (1a) above, and using in place of 2-(o-tolyl)-2-(1H)-imidazoline, an approximately equivalent amount of 2-(4-chloro-2-tolyl)-2(1H)-imidazoline, and using in place of the ethyl-p-fluorobenzoate, an approximately equivalent amount of methyl-p-(3,4,5-trimethoxyphenylethyl)-benzoate, there was obtained 8-chloro-5-[4'-(3,4,5-trimethoxyphenylethyl)phenyl]-2,3,5,6-tetrahydroamidazo[2,1-a]isoquinolin-5-ol.

EXAMPLE 9

Following essentially the last step of the procedure in preparing the compound of Example 1, and using in place of the compound of Example (1a), an approximately equivalent amount of the compound of Example 8, there was obtained 8-chloro-5-[4'-(3,4,5-trimethoxyphenylethyl)phenyl]-2,3-dihydromidazo[2,1-a]isoquinoline hydrochloride, m.p. 268° (dec.)
Test A-IC$_{50}$ 0.03 uM

EXAMPLE 10

Following essentially the procedure of Example (1a) above, and using in place of the ethyl-p-fluorobenzoate, an approximately equivalent amount of:

(a) methyl-p-(3,4,5-trimethoxyphenylpropyloxy)benzoate;
(b) methyl-p-(3,4,5-trimethoxyphenylhexyl)benzoate; and
(c) methyl-p-(3,4,5-trimethoxyphenylethyloxy)benzoate;
there was obtained
(A) 5-[4'-(3,4,5-trimethoxyphenylpropyloxy)phenyl]-2,3,5,6-tetrahydroimidazo[2,1-a]isoquinolin-5-ol;
(B) 5-[4'-(3,4,5-trimethoxyphenylhexyl)phenyl]-2,3,5,6-tetrahydroimidazo[2,1-a]isoquinolin-5-ol; and
(C) 5-[4'-(3,4,5-trimethoxyphenylethyloxy)phenyl]-2,3,5,6-tetrahydroimidazo[2,1-a]isoquinolin-5-ol; respectively.

EXAMPLE 11

Following essentially the last step of the procedure in preparing the compound of Example 1, and using in place of the compound of Example (1a), an approximately equivalent amount of the compounds of Examples (10A) through (10C), respectively, there was obtained:
(A) 5-[4'-(3,4,5-trimethoxyphenylpropyloxy)phenyl]-2,3-dihydroimidazo[2,1-a]isoquinoline hydrochloride, m.p. 215°-217° C. (dec);
(B) 5-[4'-(3,4,5-trimethoxyphenylhexyl)phenyl]-2,3-dihydroimidazo[2,1-a]isoquinoline hydrochloride, m.p. 213°-215° C.; and
(C) 5-[4'-(3,4,5-trimethoxyphenylethyloxy)phenyl]-2,3-dihydroimidazo[2,1-a]isoquinoline hydrochloride, m.p. 242°-243° C.

EXAMPLE 12

Following essentially the procedure of Example (1a) above, and using in place of 2-(o-tolyl)-2-(1H)-imidazoline, an approximately equivalent amount of 4,4-dimethyl-2-(o-tolyl)-2(1H)-imidazoline, and using in place of the ethyl-p-fluorobenzoate, an approximately equivalent amount of methyl-p-(3,4,5-trimethoxyphenylethyl)-benzoate, there was obtained 2,2-dimethyl-5-[4'-(3,4,5-trimethoxyphenylethyl)phenyl]-2,3,5,6-tetrahydroimidazo[2,1-a]isoquinolin-5-ol.

EXAMPLE 13

Following essentially the last step of the procedure in preparing the compound of Example 1, and using in place of the compound of Example (1a), an approximately equivalent amount of the compound of Example 12, there was obtained 2,2-dimethyl-5-[4'-(3,4,5-trimethoxyphenylethyl)phenyl]-2,3-dihydroimidazo[2,1-a]isoquinoline hydrochloride.

Unless indicated otherwise, all of the test results set forth for compounds (3A) through (3NN), (5A)-(5C), (7A)-(7N), 9, (11A)-(11C) and 13 in Test B and Test C are at 1 hr. pre-dose.

What is claimed is:
1. A compound of formula Ia:

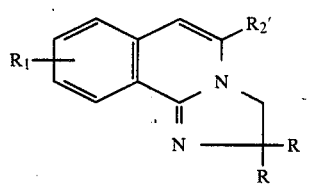

(8- or 9-)

wherein each
R, independently, is hydrogen or methyl;
$R_1$ is hydrogen, chloro, fluoro or $C_{1-3}$ alkyl; and
$R_2'$ is a member of the group selected from

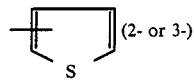 (2- or 3-)

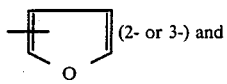 (2- or 3-) and

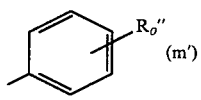 (m')

wherein
m' is an integer 1 or 2; and
$R_o''$ is straight or branched chain $C_{5-10}$ alkyl; straight or branched chain $C_{5-10}$ alkoxy; straight or branched chain $C_{5-10}$ alkylthio; tri-$C_{1-3}$ alkylsilyl; phenyl; phenyl monosubstituted by chloro or fluoro; a group of the formula

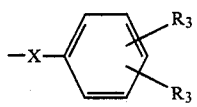

where X is —CH$_2$O—, —OCH$_2$—, —CH$_2$S—, —SCH$_2$—, —CH$_2$—, —CH$_2$CH$_2$—, —CH$_2$OCH$_2$—, —O— or —S— and each $R_3$ is hydrogen, chloro, fluoro, $C_{1-4}$alkyl or $C_{1-5}$alkoxy; a group of the formula

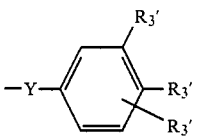

where Y is —O—(CH$_2$)$_{1-5}$, —SCH$_2$, —(CH$_2$)$_{1-6}$ or —CH$_2$OCH$_2$— and each $R_3^1$ is $C_{1-3}$ alkoxy; a group of the formula

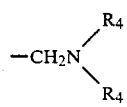

where each $R_4$, independently, is straight or branched chain $C_{1-4}$ alkyl, $C_{5-7}$ cycloalkyl, CH$_2$CH=CH$_2$, a group of the formula

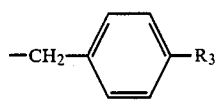

where $R_3$ is as defined above, or the two $R_4$'s together with the nitrogen atom to which they are attached form a group of the formula

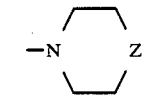

where n is an integer 4, 5 or 6, or a group of the formula

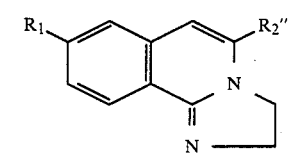

where Z is —O—, —S— or NCH$_3$; or two $R_o'''$'s on adjacent carbon atoms form methylenedioxy; with the provisos that:
(1) when $R_o''$ is other than straight or branched chain $C_{5-10}$ alkyl, alkoxy or alkylthio, m' is 1; and
(2) the $R_o''$ substituent(s) may only be in the meta or para positions;
or a pharmaceutically acceptable acid addition salt thereof.

2. A compound according to claim 1 of formula Ia':

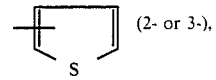 Ia' where
$R_1$ is as defined in claim 1; and
$R_2''$ is a member of the group selected from

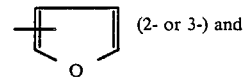 (2- or 3-),

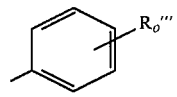 (2- or 3-) and

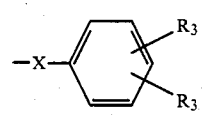

where $R_o'''$ is tri-$C_{1-3}$ alkylsilyl; a group of the formula

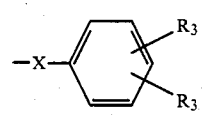

where X and each $R_3$ are as defined in claim 1; a group of the formula

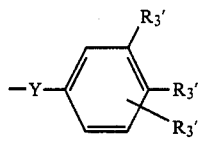

where Y and each $R_3'$ are as defined in claim 1; or a group of the formula

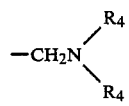

where each $R_4$, independently, is as defined in claim 1; with the proviso that the $R_o'''$ substitutent may only be in the meta or para positions; or a pharmaceutically acceptable acid addition salt thereof.

3. A compound according to claim 2 having the formula

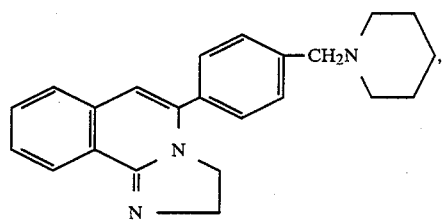

or a pharmaceutically acceptable acid addition salt thereof.

4. A compound according to claim 2 having the formula

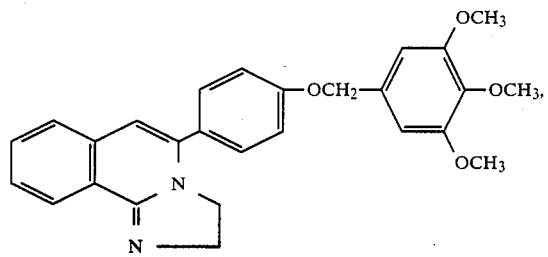

or a pharmaceutically acceptable acid addition salt thereof.

5. A compound according to claim 4 having the formula

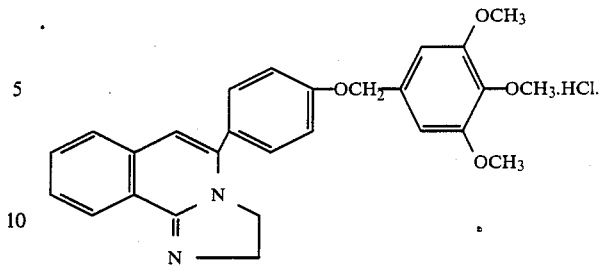

6. A compound according to claim 2 having the formula

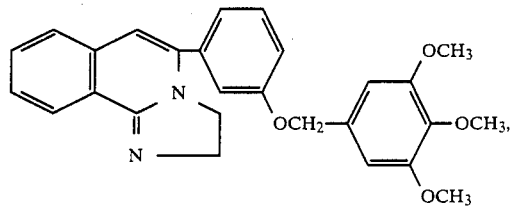

or a pharmaceutically acceptable acid addition salt thereof.

7. A compound according to clam 6 having the formula

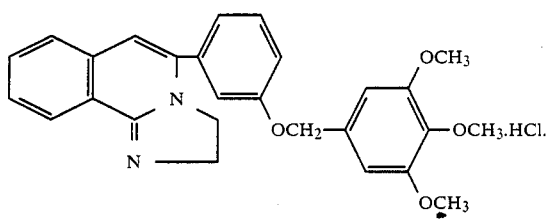

8. A compound according to claim 2 having the formula

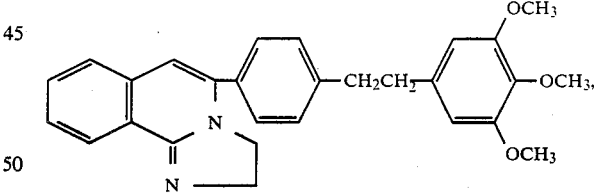

or a pharmaceutically acceptable acid addition salt thereof.

9. A compound according to claim 8 having the formula

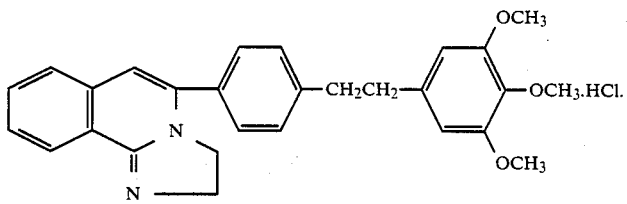

10. A compound according to claim 2 having the formula

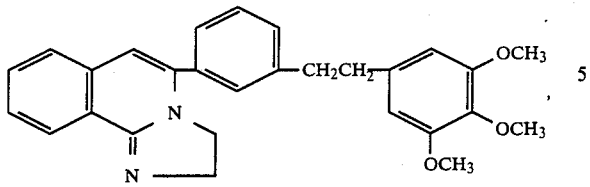

or a pharmaceutically acceptable acid additional salt thereof.

11. A compound according to claim 10 having the formula

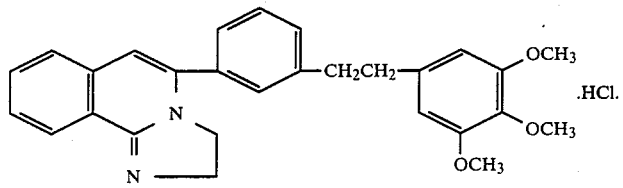

12. A pharmaceutical composition useful in inhibiting PAF-mediated bromchoconstriction and extravasation, PAF-mediated endotoxin-induced lung injury and for controlling hyperreactive airways induced by PAF or allergen comprising a pharmaceutically acceptable carrier and a therapeutically effective amount of a compound of claim 1, or a pharmaceutically acceptable acid addition salt thereof.

13. A method of inhibiting PAF mediated bronchoconstriction and extravasation comprising administering to a subject afflicted therewith a therapeutically effective amount of a compound of formula I:

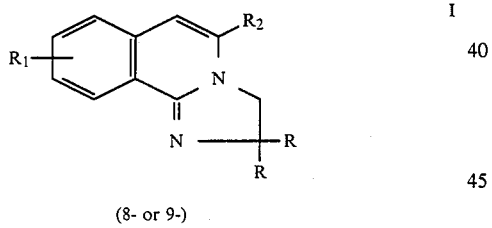

(8- or 9-)

wherein each
R, independently, is hydrogen or methyl;
$R_1$ is hydrogen, chloro, fluoro or $C_{1-3}$ alkyl; and
$R_2$ is a member of the group selected from

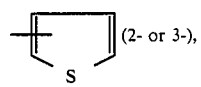 (2- or 3-),

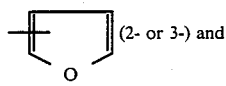 (2- or 3-) and

 (m)

where
m is 0 or an integer 1 or 2; and $R_o$ is chloro; fluoro; straight or branched chain $C_{1-10}$ alkyl; straight or branched chain $C_{1-10}$ alkoxy; straight or branched chain $C_{1-10}$ alkylthio; tri-$C_{1-3}$alkylsilyl; trifluoromethyl; phenyl; phenyl monosubstituted by chloro or fluoro; a group of the formula

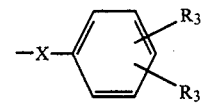

where X is —CH$_2$O—, —OCH$_2$—, —CH$_2$S—, —SCH$_2$—, —CH$_2$—, —CH$_2$CH$_2$—, —CH$_2$OCH$_2$—, —O— or —S— and each $R_3$ is hydrogen, chloro, fluoro, $C_{1-4}$ alkyl or $C_{1-5}$ alkoxy; a group of the formula

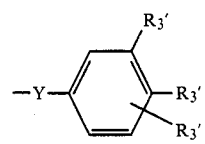

where Y is —O—(CH$_2$)$_{1-5}$, —SCH$_2$—, —(CH$_2$)$_{1-6}$ or —CH$_2$OCH$_2$— and each $R_3'$ is $C_{1-3}$ alkoxy; a group of the formula

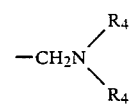

where each $R_4$, independently, is straight or branched chain $C_{1-4}$ alkyl, $C_{5-7}$ cycloalkyl, CH$_2$CH=CH$_2$, a group of the formula

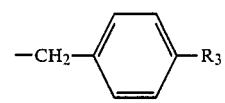

where $R_3$ is as defined above, or the two $R_4$'s together with the nitrogen atom to which they are attached form a group of the formula

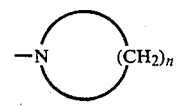

where n is an integer 4, 5 or 6, or a group of the formula

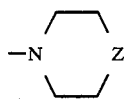

where Z is —O—, —S— or —NCH₃; or two R$_o$'s on adjacent carbon atoms form methylenedioxy; with the provisos that: (1) when R$_o$ is other than chloro, fluoro, or straight or branched chain C$_{1-10}$ alkyl, alkoxy or alkylthio, m is 1; (2) when R$_o$ is other than chloro, fluoro, methyl, methoxy or methylthio, the R$_o$ substituent(s) may only be in the meta or para positions;
or a pharmaceutically acceptable acid addition salt thereof.

14. A method according to claim 13 wherein the compound administered is of formula I':

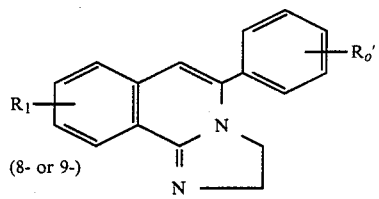

wherein
R$_1$ is as defined in claim 13; and
R$_o$' is a group of the formula

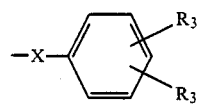

where X and each R$_3$ are as defined in claim 13; or a group of the formula

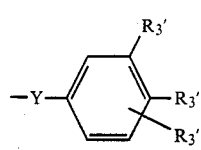

where Y and each R$_3$' are as defined in claim 13; with the proviso that the R$_o$' substituent may only be in the meta or para positions;
or a pharmaceutically acceptable acid addition salt thereof.

15. A method according to claim 14 wherein the compound administered is of the formula

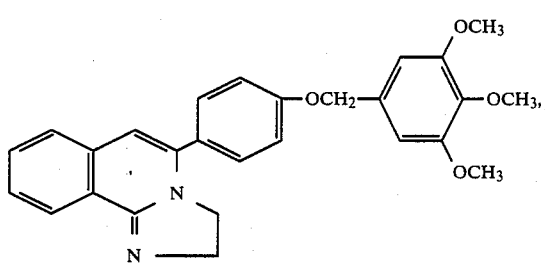

or a pharmaceutically acceptable acid addition salt thereof.

16. A method according to claim 15 wherein the compound administered is of the formula

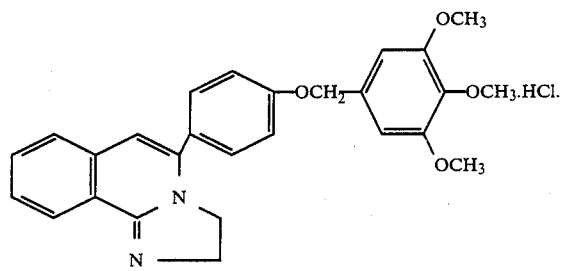

17. A method according to claim 14 wherein the compound administered is of the formula

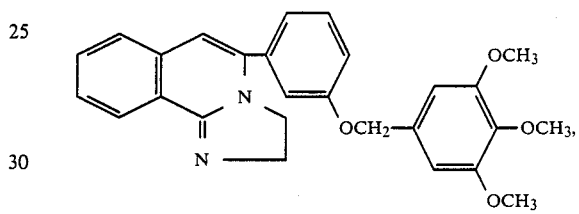

or a pharmaceutically acceptable acid addition salt thereof.

18. A method according to claim 17 wherein the compound administered is of the formula

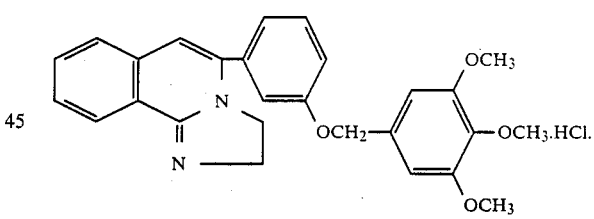

19. A method according to claim 14 wherein the compound administered is of the formula

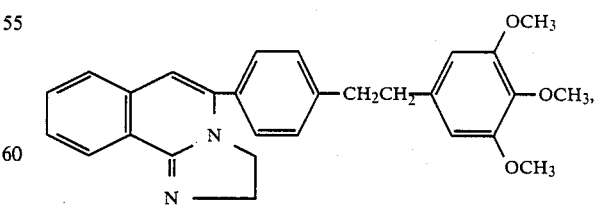

or a pharmaceutically acceptable acid addition salt thereof.

20. A method according to claim 19 wherein the compound administered is of the formula

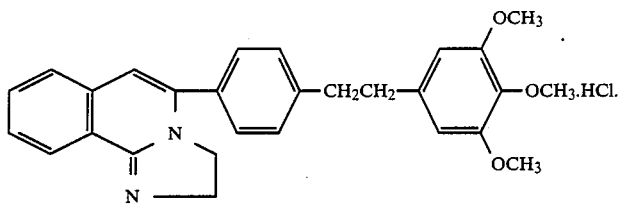

21. A method according to claim 14 wherein the compound administered is of the formula

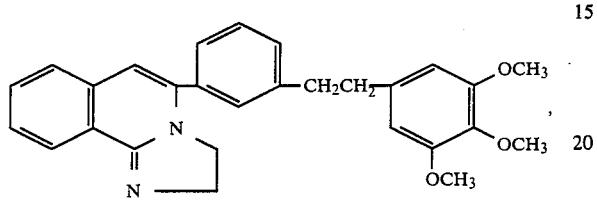

or a pharmaceutically acceptable acid addition salt thereof.

22. A method according to claim 21 wherein the compound administered is of the formula

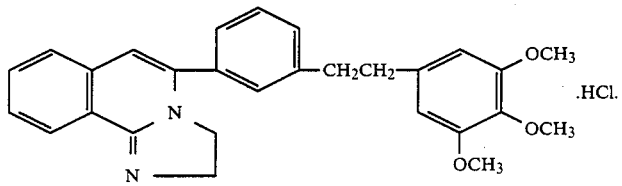

23. A method of inhibiting PAF-mediated, endotoxin-induced lung injury comprising administering to a subject afflicted therewith a therapeutically effective amount of a compound of formula I:

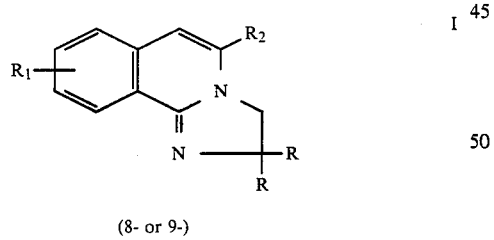

(8- or 9-)

wherein each
R, independently, is hydrogen or methyl;
$R_1$ is hydrogen, chloro, fluoro or $C_{1-3}$ alkyl; and
$R_2$ is a member of the group selected from

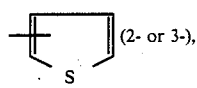 (2- or 3-),

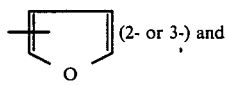 (2- or 3-) and

-continued

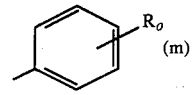

where
m is 0 or an integer 1 or 2; and
$R_o$ is chloro; fluoro; straight or branched chain $C_{1-10}$ alkyl; straight or branched chain $C_{1-10}$ alkoxy; straight or branched chain $C_{1-10}$ alkylthio; tri-$C_{1-3}$-alkylsilyl; trifluoromethyl; phenyl; phenyl monosubstituted by chloro or fluoro; a group of the formula

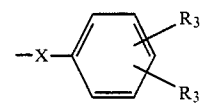

where X is —CH$_2$O—, —OCH$_2$—, —CH$_2$S—, —SCH$_2$—, —CH$_2$—, —CH$_2$CH$_2$—, —CH$_2$OCH$_2$—, —O— or —S— and each $R_3$ is hydrogen, chloro, fluoro, $C_{1-4}$alkyl or $C_{1-5}$ alkoxy; a group of the formula

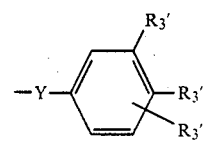

where Y is —O—(CH$_2$)$_{1-5}$, —SCH$_2$—, —(CH$_2$)$_{1-6}$ or —CH$_2$OCH$_2$— and each $R_3'$ is $C_{1-3}$ alkoxy; a group of the formula

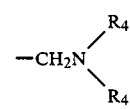

where each $R_4$, independently, is straight or branched chain $C_{1-4}$ alkyl, $C_{5-7}$ cycloalkyl, CH$_2$CH=CH$_2$, a group of the formula

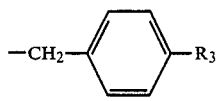

where R₃ is as defined above, or the two R₄'s together with the nitrogen atom to which they are attached form a group of the formula

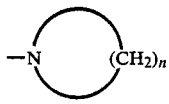

where n is an integer 4, 5 or 6, or a group of the formula

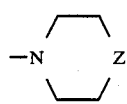

where Z is —O—, —S— or —NCH₃; or two $R_o$'s on adjacent carbon atoms form methylenedioxy; with the provisos that: (1) when $R_o$ is other than chloro, fluoro, or straight or branched chain $C_{1-10}$ alkyl, alkoxy or alkylthio, m is 1; (2) when $R_o$ is other than chloro, fluoro, methyl, methoxy or methylthio, the $R_o$ substituent(s) may only be in the meta or para positions;
or a pharmaceutically acceptable acid addition salt thereof.

24. A method according to claim 23 wherein the compound administered is of formula I':

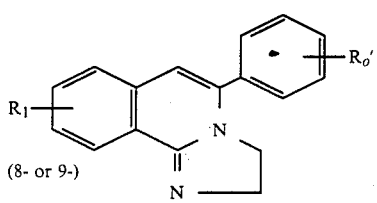

wherein
R₁ is as defined in claim 23; and
$R_o'$ is a group of the formula

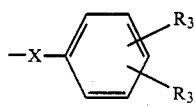

where X and each R₃ are as defined in claim 23; or a group of the formula

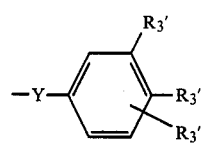

where Y and each R₃' are as defined in claim 23; with the proviso that the $R_o'$ substituent may only be in the meta or para positions;

or a pharmaceutically acceptable acid addition salt thereof.

25. A method according to claim 24 wherein the compound administered is of the formula

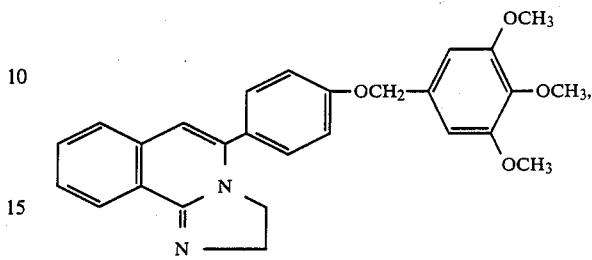

or a pharmaceutically acceptable acid addition salt thereof.

26. A method according to claim 25 wherein the compound administered is of the formula

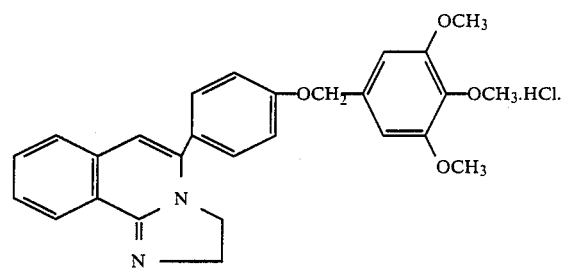

27. A method according to claim 24 wherein the compound administered is of the formula

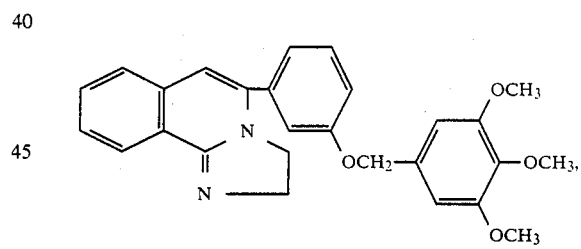

or a pharmaceutically acceptable acid addition salt thereof.

28. A method according to claim 27 wherein the compound administered is of the formula

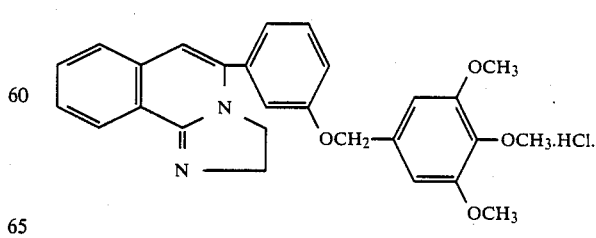

29. A method according to claim 24 wherein the compound administered is of the formula

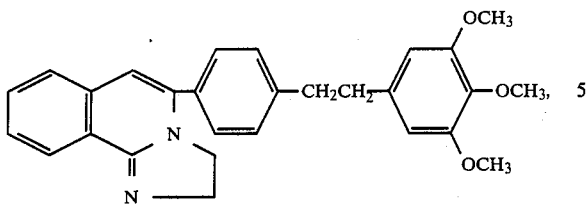

or a pharmaceutically acceptable acid addition salt thereof.

30. A method according to claim 29 wherein the compound administered is of the formula

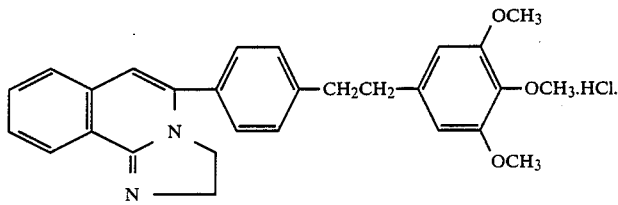

31. A method according to claim 24 wherein the compound administered is of the formula

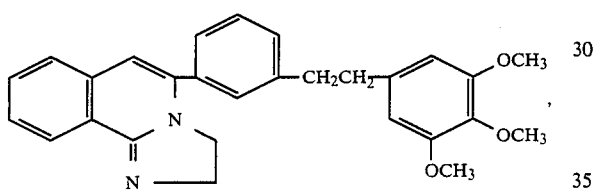

or a pharmaceutically acceptable acid addition salt thereof.

32. A method according to claim 31 wherein the compound administered is of the formula

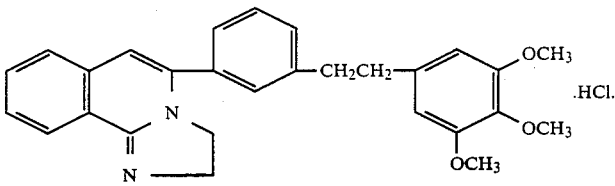

33. A method of controlling hyperreactive airways induced by PAF or allergen comprising administering to a subject afflicted therewith a therapeutically effective amount of a compound of formula I:

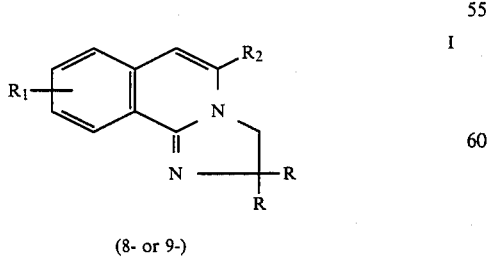

wherein each
   R, independently, is hydrogen or methyl;
   $R_1$ is hydrogen, chloro, fluoro or $C_{1-3}$ alkyl; and $R_2$ is a member of the group selected from

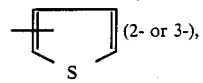 (2- or 3-),

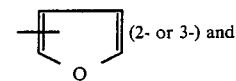 (2- or 3-) and

 (m)

where
m is 0 or an integer 1 or 2; and
$R_o$ is chloro; fluoro; straight or branched chain $C_{1-10}$ alkyl; straight or branched chain $C_{1-10}$ alkoxy; straight or branched chain $C_{1-10}$ alkylthio; tri-$C_{1-3}$-alkylsilyl; trifluoromethyl; phenyl; phenyl monosubstituted by chloro or fluoro; a group of the formula

where X is —$CH_2O$—, —$OCH_2$—, —$CH_2S$—, —$SCH_2$—, —$CH_2$—, —$CH_2CH_2$—, —$CH_2OCH_2$—, —O— or —S— and each $R_3$ is hydrogen, chloro, fluoro, $C_{1-4}$alkyl or $C_{1-5}$alkoxy; a group of the formula

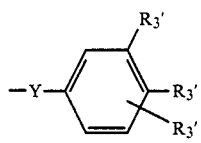

where Y is —O—$(CH_2)_{1-5}$, —$SCH_2$—, —$(CH_2)_{1-6}$ or —$CH_2OCH_2$— and each $R_3'$ is $C_{1-3}$ alkoxy; a group of the formula

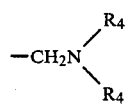

where each $R_4$, independently, is straight or branched chain $C_{1-4}$ alkyl, $C_{5-7}$ cycloalkyl, $CH_2CH=CH_2$, a group of the formula

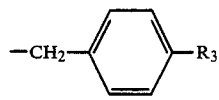

where $R_3$ is as defined above, or the two $R_4$'s together with the nitrogen atom to which they are attached form a group of the formula

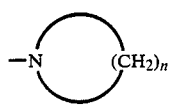

where n is an integer 4, 5 or 6, or a group of the formula

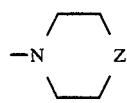

where Z is $-O-$, $-S-$ or $-NCH_3$; or two $R_o$'s on adjacent carbon atoms form methylenedioxy; with the provisos that: (1) when $R_o$ is other than chloro, fluoro, or straight or branched chain $C_{1-10}$ alkyl, alkoxy or alkylthio, m is 1; (2) when $R_o$ is other than chloro, fluoro, methyl, methoxy or methylthio, the $R_o$ substituent(s) may only be in the meta or para positions;
or a pharmaceutically acceptable acid addition salt thereof.

34. A method according to claim 33 wherein the compound administered is of formula I':

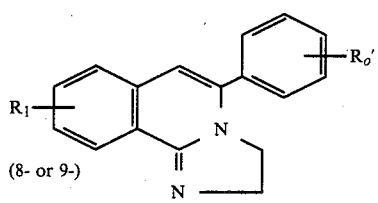

wherein
$R_1$ is as defined in claim 33; and $R_o'$ is a group of the formula

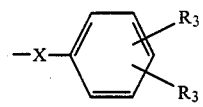

where X and each $R_3$ are as defined in claim 33; or a group of the formula

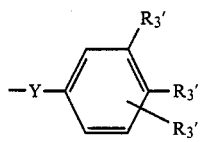

where Y and each $R_3'$ are as defined in claim 33; with the proviso that the $R_o'$ substituent may only be in the meta or para positions;
or a pharmaceutically acceptable acid addition salt thereof.

35. A method according to claim 34 wherein the compound administered is of the formula

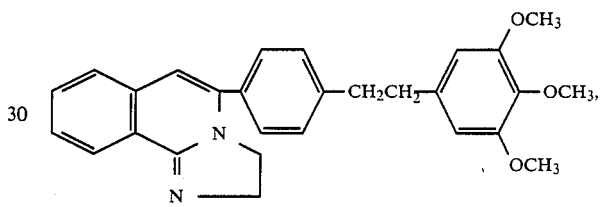

or a pharmaceutically acceptable acid addition salt thereof.

36. A method according to claim 35 wherein the compound administered is of the formula

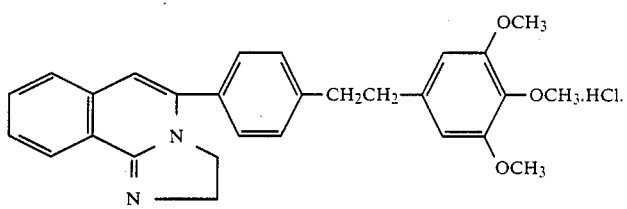

37. A method according to claim 33 wherein a compound of formula I, or a pharmaceutically acceptable acid addition salt, is administered to a subject by the inhalation route.

38. A method according to claim 37 wherein the compound administered is of the formula

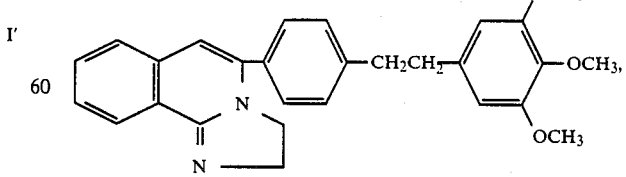

or a pharmaceutically acceptable acid addition salt thereof.

39. A method according to claim 38 wherein the compound administered is of the formula

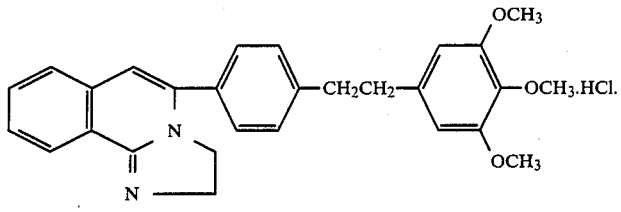

40. A method of treating tumors comprising administering to a subject afflicted therewith a therapeutically effective amount of a compound of formula Ib:

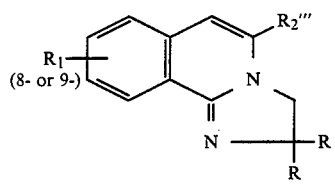

wherein each
R, independently, is hydrogen or methyl;
$R_1$ is hydrogen, chloro, fluoro or $C_{1-3}$alkyl;
$R_2'''$ is a member of the group selected from

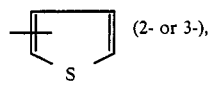 (2- or 3-),

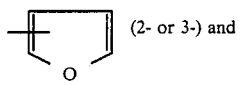 (2- or 3-) and

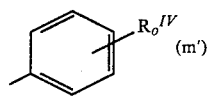 (m')

where m' is an integer 1 or 2;
$R_o^{IV}$ is chloro; fluoro; straight or branched chain $C_{1-6}$alkyl; tri-$C_{1-3}$alkylsilyl; phenyl; a group of the formula

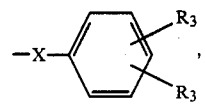

where X is —CH$_2$O—, —OCH$_2$—, —CH$_2$S—, —SCH$_2$—, —CH$_2$—, —CH$_2$CH$_2$—, —CH$_2$OCH$_2$—, —O— or —S— and each $R_3$ is hydrogen, chloro, fluoro or $C_{1-4}$alkyl or $C_{1-5}$alkoxy; a group of the formula

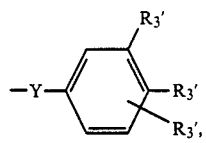

where Y is —O-(CH$_2$)$_{1-5}$, —SCH$_2$—, -(CH$_2$)$_{1-6}$ or —CH$_2$OCH$_2$— and each $R_3'$ is $C_{1-3}$alkoxy; or a group of the formula

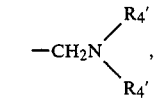

where each $R_4'$ is CH$_2$CH=CH$_2$, or the two $R_4''$s together with the nitrogen to which they are attached form a group of the formula

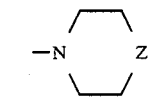

where n is an integer 4, 5 or 6, or a group of the formula

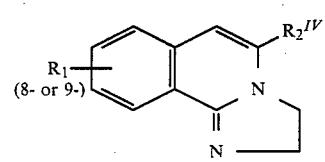

where Z is —O—, —S— or —NCH$_3$; with the provisos that:
(1) when $R_o^{IV}$ is other than chloro, fluoro or $C_{1-6}$alkyl, m' is 1; and
(2) when $R_o^{IV}$ is other than chloro, fluoro or methyl, the $R_o^{IV}$ substituent may only be in the meta or para positions;

or a pharmaceutically acceptable acid addition salt thereof.

41. A method according to claim 40 wherein the compound administered is of formula Ib':

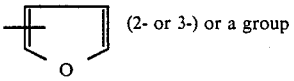

where
$R_1$ is as defined in claim 40; and
$R_2^{IV}$ is a group

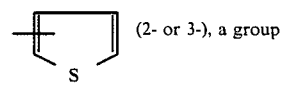 (2- or 3-), a group

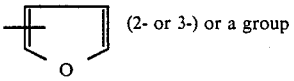 (2- or 3-) or a group

-continued

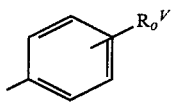

where $R_o^V$ is straight or branched chain $C_{2-6}$alkyl; tri-$C_{1-3}$alkylsilyl; phenyl; a group of the formula

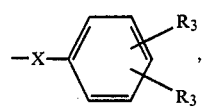

where X and each $R_3$ are as defined in claim 40; a group of the formula

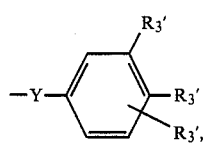

where Y and each $R_3'$ are as defined in claim 40; or a group of the formula

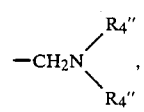

where each $R_4''$ is $CH_2CH=CH_2$, or the two $R_4'''$'s together with the nitrogen to which they are attached form a group of the formula

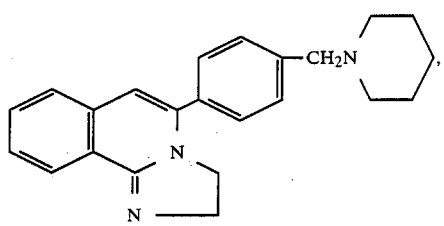

where n is as defined in claim 40; with the proviso that the $R_o^V$ substituent may only be in the meta or para positions;

or a pharmaceutically acceptable acid addition salt thereof.

42. A method according to claim 41 wherein the compound administered is of the formula

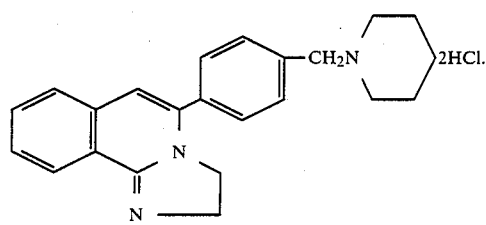

or a pharmaceutically acceptable acid addition salt thereof.

43. A method according to claim 42 wherein the compound administered is of the formula

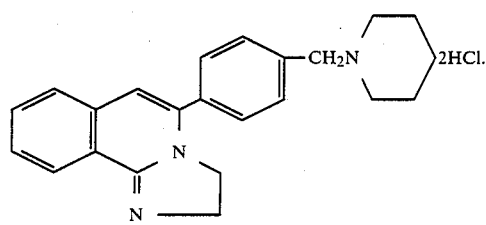

* * * * *